(12) United States Patent
Merzenich et al.

(10) Patent No.: US 8,215,961 B2
(45) Date of Patent: Jul. 10, 2012

(54) COGNITIVE TRAINING USING VISUAL SWEEPS

(75) Inventors: Michael M. Merzenich, San Francisco, CA (US); Peter B. Delahunt, San Mateo, CA (US); Joseph L. Hardy, Richmond, CA (US); Stephen G. Lisberger, San Francisco, CA (US); Henry W. Mahncke, San Francisco, CA (US)

(73) Assignee: Posit Science Corporation, San Francisco, CA (US)

( * ) Notice: Subject to any disclaimer, the term of this patent is extended or adjusted under 35 U.S.C. 154(b) by 808 days.

(21) Appl. No.: 11/611,225

(22) Filed: Dec. 15, 2006

(65) Prior Publication Data

US 2007/0293732 A1 Dec. 20, 2007

Related U.S. Application Data

(60) Provisional application No. 60/750,509, filed on Dec. 15, 2005, provisional application No. 60/762,432, filed on Jan. 26, 2006, provisional application No. 60/746,406, filed on May 4, 2006.

(51) Int. Cl.
*G09B 19/00* (2006.01)

(52) U.S. Cl. .......................................... 434/236; 434/350

(58) Field of Classification Search ................... 434/236, 434/258, 322–365; 600/300–301, 544, 558, 600/595; 351/203, 209, 222, 224, 226, 237, 351/239, 246

See application file for complete search history.

(56) References Cited

U.S. PATENT DOCUMENTS

| | | | |
|---|---|---|---|
| 4,971,434 A | 11/1990 | Ball | |
| 5,801,810 A | 9/1998 | Roenker | |
| 6,328,569 B1 | 12/2001 | Jenkins et al. | |
| 6,334,777 B1 | 1/2002 | Jenkins et al. | |
| 6,364,486 B1 | 4/2002 | Ball et al. | |
| 6,413,098 B1 | 7/2002 | Tallal et al. | |
| 6,464,356 B1 | 10/2002 | Sabel et al. | |
| 6,585,519 B1 | 7/2003 | Jenkins et al. | |

(Continued)

FOREIGN PATENT DOCUMENTS

DE 69529054 8/2003

(Continued)

OTHER PUBLICATIONS

Sekuler et al. "Visual localization: age and practice." Optical Society of America. vol. 3, No. 6. Jun. 1986. pp. 864-867.

(Continued)

*Primary Examiner* — Timothy A Musselman
(74) *Attorney, Agent, or Firm* — James W. Huffman

(57) ABSTRACT

A computer-implemented method for enhancing cognitive ability of an older participant by requiring the participant to differentiate between rapidly presented visual stimuli. First and second visual sweeps are provided for visual presentation to the participant, e.g., spatial frequency or orientation sweeps. At least two visual sweeps are visually presented to the participant utilizing the first visual sweep, the second visual sweep, or a combination. The participant is required to indicate an order in which the at least two visual sweeps were presented. A determination is made regarding whether the participant indicated the order of the visual sweeps correctly. The visually presenting, requiring, and determining are repeated one or more times in an iterative manner to improve the participant's cognition. The duration of the sweeps may be adjusted based on the correctness/incorrectness of the participant's response according to a maximum likelihood procedure. Assessments may be made during the exercise.

45 Claims, 16 Drawing Sheets

U.S. PATENT DOCUMENTS

| | | | |
|---|---|---|---|
| 6,599,129 | B2 | 7/2003 | Jenkins et al. |
| 6,626,676 | B2 | 9/2003 | Freer |
| 7,367,675 | B2 * | 5/2008 | Maddalena et al. .......... 351/237 |
| 7,549,743 | B2 * | 6/2009 | Huxlin et al. ................. 351/203 |
| 2003/0201982 | A1 | 10/2003 | Iesaka |
| 2005/0175972 | A1 * | 8/2005 | Goldman et al. ............. 434/236 |
| 2005/0213033 | A1 | 9/2005 | Sabel |
| 2006/0161218 | A1 | 7/2006 | Danilov |
| 2006/0234199 | A1 | 10/2006 | Walker et al. |
| 2007/0166675 | A1 | 7/2007 | Atkins et al. |
| 2007/0166676 | A1 | 7/2007 | Bird et al. |
| 2007/0218439 | A1 | 9/2007 | Delahunt et al. |
| 2007/0218440 | A1 | 9/2007 | Delahunt et al. |
| 2007/0218441 | A1 | 9/2007 | Delahunt et al. |
| 2008/0084427 | A1 | 4/2008 | Delahunt et al. |

FOREIGN PATENT DOCUMENTS

| | | |
|---|---|---|
| EP | 00502984 | 12/1992 |
| EP | 1069855 | 8/2001 |
| WO | WO 9952419 | 10/1999 |
| WO | WO03065964 | 8/2003 |

OTHER PUBLICATIONS

Ball et al. "Effects of Cognitive Training Interventions With Older Adults: A Randomized Controlled Trial." American Medical Association. Nov. 13, 2002. vol. 288, No. 18. pp. 2271-2281.

Su et al. "De-Emphasis of Distracting Image Regions Using Texture Power Maps." Computer Science and Artificial Intelligence Laboratory Technical Report. Apr. 12, 2005. pp. 1-12. Web Sep. 21, 2009. http://dspace.mit.edu/handle/1721.1/30537.

Phipps et al. "Fast Psychophysical Procedures for Clinical Testing." Clinical and Experimental Optometry 84.5 pp. 264-269. QUP ePrints. May 4, 2007. Web Sep. 21, 2009, http://eprints.qut.edu.au/7481.

Campanella, S. et al. "Association of the Distinct Visual Representations of Faces and Names: A PET Activation Study." NeuroImage 14, 873-882 (2001) pp. 1-4.

Schweinberger, Stefan R. et al. "Human Brain Potential Correlates of Repetition Priming in Face and Name Recognition." University of Glasgow; Neuropsychologia 40 (2002) 2057-2073.

Pylyshyn, Zenon W. "Visual Indexes, Preconceptual Objects, and Situated Vision." Cognition 80 (2001) 127-158 Rutgers Center for Cognitive Science, Rutgers University, Psychology Building, New Wing, Busch Campus, New Brunswick, NJ 08903.

Baudouin, Jean-Yves et al. "Selective Attention to Facial Emotion and Identity in Schizophrenia." Neuropsychologia 40 (2002) 503-511.

Wallace, Marcie A et al. "Savings in Relearning Face-Name Associations as Evidence for 'Covert Recognition' in Prosopagnosia." ONR Technical Report, Jan. 1992. Department of Psychology, Carnegie Mellon University, Pittsburgh, PA 15213. pp. 1-17.

Herholz, Karl et al. "Learning Face-Name Associations and the Effect of Age and Performance: A PET Activation Study." Neuropsychologia 39 (2001) 643-650.

* cited by examiner

COGNITIVE TRAINING USING VISUAL SWEEPS

CROSS REFERENCE TO RELATED APPLICATION(S)

This application claims the benefit of the following US Provisional Patent Applications, which are incorporated herein in their entirety for all purposes:

| Ser. No. | Filing Date: | Title: |
| --- | --- | --- |
| 60/750,509 | Dec. 15, 2005 | HAWKEYE ASSESSMENTS SPECIFICATION |
| 60/762,432 | Jan. 26, 2006 | COMPUTER BASED TRAINING PROGRAM TO REVERSE AGE RELATED DECLINES IN SPATIAL AND TEMPORAL PROCESSING OF VISUAL STIMULI |
| 60/746,406 | May 4, 2006 | COMPUTER BASED TRAINING PROGRAM TO REVERSE AGE RELATED DECLINES IN VISUAL SEARCH |

The following applications are related to the present application:

| | | |
| --- | --- | --- |
| 11/611,232 | Dec. 15, 2006 | COGNITIVE TRAINING USING VISUAL SEARCHES |
| 11/611,241 | Dec. 15, 2006 | COGNITIVE TRAINING USING MULTIPLE OBJECT TRACKING |
| 11/611,252 | Dec. 15, 2006 | COGNITIVE TRAINING USING FACE-NAME ASSOCIATIONS |
| 11/611,329 | Dec. 15, 2006 | COGNITIVE TRAINING USING EYE MOVEMENT |
| 11/611,291 | Dec. 15, 2006 | COGNITIVE TRAINING USING VISUAL STIMULI |
| 11/611,318 | Dec. 15, 2006 | VISUAL EMPHASIS FOR COGNITIVE TRAINING |

FIELD OF THE INVENTION

This invention relates in general to the use of brain health programs utilizing brain plasticity to enhance human performance and correct neurological disorders, and more specifically, to a method for improving the ability of the visual nervous system to accurately encode information about multiple visual events of short duration.

BACKGROUND OF THE INVENTION

Almost every individual has a measurable deterioration of cognitive abilities as he or she ages. The experience of this decline may begin with occasional lapses in memory in one's thirties, such as increasing difficulty in remembering names and faces, and often progresses to more frequent lapses as one ages in which there is passing difficulty recalling the names of objects, or remembering a sequence of instructions to follow directions from one place to another. Typically, such decline accelerates in one's fifties and over subsequent decades, such that these lapses become noticeably more frequent. This is commonly dismissed as simply "a senior moment" or "getting older." In reality, this decline is to be expected and is predictable. It is often clinically referred to as "age-related cognitive decline," or "age-associated memory impairment." While often viewed (especially against more serious illnesses) as benign, such predictable age-related cognitive decline can severely alter quality of life by making daily tasks (e.g., driving a car, remembering the names of old friends) difficult.

As a more specific example, it is believed that the visual systems of older adults suffer from a degraded ability to accurately and efficiently represent rapidly presented successive stimuli. As a consequence of this inability, events that occur close together in time are not properly represented as separate events. For example, if a small object is presented at time 1 and a large object is presented at time 2 and the individual is asked to reconstruct the order of presentation, older individuals will generally be less accurate than younger individuals when presentation times and inter-stimulus intervals are brief. Being able to quickly and accurately encode visual information is critical to day-to-day living. For example, driving a car demands continual accurate and rapid extraction of multiple visual events.

In many older adults, age-related cognitive decline leads to a more severe condition now known as Mild Cognitive Impairment (MCI), in which sufferers show specific sharp declines in cognitive function relative to their historical lifetime abilities while not meeting the formal clinical criteria for dementia. MCI is now recognized to be a likely prodromal condition to Alzheimer's Disease (AD) which represents the final collapse of cognitive abilities in an older adult. The development of novel therapies to prevent the onset of this devastating neurological disorder is a key goal for modern medical science.

The majority of the experimental efforts directed toward developing new strategies for ameliorating the cognitive and memory impacts of aging have focused on blocking and possibly reversing the pathological processes associated with the physical deterioration of the brain. However, the positive benefits provided by available therapeutic approaches (most notably, the cholinesterase inhibitors) have been modest to date in AD, and are not approved for earlier stages of memory and cognitive loss such as age-related cognitive decline and MCI.

Cognitive training is another potentially potent therapeutic approach to the problems of age-related cognitive decline, MCI, and AD. This approach typically employs computer- or clinician-guided training to teach subjects cognitive strategies to mitigate their memory loss. Although moderate gains in memory and cognitive abilities have been recorded with cognitive training, the general applicability of this approach has been significantly limited by two factors: 1) Lack of Generalization; and 2) Lack of enduring effect.

Lack of Generalization: Training benefits typically do not generalize beyond the trained skills to other types of cognitive tasks or to other "real-world" behavioral abilities. As a result, effecting significant changes in overall cognitive status would require exhaustive training of all relevant abilities, which is typically infeasible given time constraints on training.

Lack of Enduring Effect: Training benefits generally do not endure for significant periods of time following the end of training. As a result, cognitive training has appeared infeasible given the time available for training sessions, particularly from people who suffer only early cognitive impairments and may still be quite busy with daily activities.

As a result of overall moderate efficacy, lack of generalization, and lack of enduring effect, no cognitive training strategies are broadly applied to the problems of age-related cognitive decline, and to date they have had negligible commercial impacts. The applicants believe that a significantly innovative type of training can be developed that will surmount these challenges and lead to fundamental improvements in the treatment of age-related cognitive decline. This innovation is based on a deep understanding of the science of "brain plasticity" that has emerged from basic research in neuroscience over the past twenty years, which only now through the application of computer technology can be brought out of the laboratory and into the everyday therapeutic treatment.

Thus, improved systems and methods for improving the ability of the visual nervous system to accurately encode information about multiple visual events of short duration are desired.

SUMMARY

Various embodiments are presented of a system and method implementing a cognitive training exercise that utilizes visual sweeps, e.g., of spatial frequency and/or orientation patterns, to improve cognition of a participant, e.g., an aging adult. Two exemplary tasks using such visual sweeps are first described, after which the general exercise is described. It should be noted that various embodiments of the visual sweep tasks described herein, or other visual sweep tasks, may be used singly or in combination in the exercise. Moreover, as described below, in some embodiments, stimulus threshold assessments may also be performed in conjunction with, or as part of, the exercise, thus facilitating more effective training of the participant's cognitive system.

Note that in preferred embodiments, the exercise may be presented in the context of a game (or games). In other words, the visual sweep exercise(s) described herein may be implemented, embedded, or encapsulated, in a game, where the game elements, although not necessarily related to the particular task(s) of the exercise (e.g., the visual sweeps), may provide mechanisms for engaging the participant, and keeping the participant engaged and interested in progressing through the exercise, e.g., by providing a reward structure, progress cues, and so forth.

The two tasks described below visually present spatial frequency patterns to a participant, and receive input from the participant in response that characterizes the patterns in some way, such as the direction of a frequency sweep (Task 1) or a changing orientation of the pattern (Task 2), although in other embodiments, other visual sweep tasks may also be utilized. Difficulty on these tasks may be manipulated by adjusting the durations of the stimulus presentations/ISI, as will be described in detail below. These tasks may be performed singly or in combination in the visual sweep exercise, described below.

Task 1: Spatial Frequency Sweep Time Order Judgment

In this task, the participant may perform a time order judgment task in which he or she is required to indicate for each of two time intervals whether a presented spatial frequency pattern was expanding or contracting in spatial frequency. Spatial frequency is a characteristic of how a pattern repeats itself over space. For a pattern made up of bars, the wider the bars, the lower the spatial frequency. A sweep of spatial frequency in the visual domain is analogous to an FM (frequency modulation) sweep in the auditory domain.

In a preferred embodiment, stimuli for the task may be sine wave modulated gratings that change in spatial frequency over time, although in other embodiments, other frequency patterns may be used as desired, e.g., concentric circles, stark black and white bars, etc. A sine wave modulated grating is a pattern that varies in luminance (roughly equivalent to the phenomenal experience of lightness) as a sine function of space along a particular dimension. A horizontal sine wave grating varies in luminance as a function of the y-dimension of space. A vertical sine wave grating varies in luminance as a function of the x-dimension of space. It should be noted that sine wave gratings can appear at any orientation.

The gratings may be windowed by a 2-dimensional Gaussian to remove sharp edges which otherwise introduce high spatial frequency intrusions. This windowed pattern is referred to as a Gabor stimulus. The frequency of the modulation over space (the spatial frequency) is inversely related to the distance between the luminance peaks (the white stripes), i.e., the "wavelength" of the pattern. The frequency of each Gabor pattern may be represented in cycles (wavelengths) per degree, e.g., c/deg, where the determination of spatial frequency in cycles per degree depends on the distance of the observer from the screen. In one embodiment, the color of the presented patterns may vary pseudo-randomly from trial to trial among colors that map to distinct points in a physiologically motivated chromaticity space (cone contrast space).

In some embodiments, during the course of the task, patterns may be presented at various orientations, e.g., at 4 orientations: 90 deg (vertical), 0 deg (horizontal), 45 deg (diagonal 1), and 135 deg (diagonal 2), although other orientations may be used as desired (although this should not be confused with Task 2, described below). The contrast of the gratings may be set at 75%, e.g., using the well-known Michelson calculation method. Additionally, the pixels values may be gamma corrected, e.g., using a gamma value of 2.2.

Task 2: Orientation Sweep Time Order Judgment

In this task, the participant may perform a time order judgment task in which he or she may be required to indicate for each of two or more orientation sweeps whether the pattern was rotating clockwise or counterclockwise. In other words, two or more spatial frequency patterns may be presented in succession, where during each presentation, the pattern is rotated at a specified rate through a specified angle, after which the participant may be required to indicate, in order, the rotation direction of each pattern, e.g., clockwise (CW) or counter-clockwise (CCW). By engaging participants repetitively in such an identification task, more precise and temporally segregated representations of orientation and change in orientation in the visual cortex may be facilitated.

In a preferred embodiment, stimuli for this task may be Gabor patterns that change in orientation over time (see Task 1 discussion above for a description of Gabor patterns), although, as with the spatial frequency sweep task described above, in other embodiments, other patterns may be used as desired. Orientations may be specified in terms of degrees (0-360°), although other units, such as radians, may be used as desired. An orientation of 0° may represent a horizontal pattern, while 90° may correspond to a vertical pattern.

The following describes embodiments of a method for cognitive training using visual sweeps. More specifically, the method utilizes a computing device to present visual sweeps, such as, for example, spatial frequency and/or orientation sweeps, for training, and to record responses from the participant. The method may be performed as follows:

First and second visual sweeps may be provided for visual presentation to the participant. For example, the first and second visual sweeps may be spatial frequency sweeps, or orientation sweeps, although other types of visual sweeps may also be used as desired.

At least two visual sweeps may be visually presented to the participant utilizing either the first visual sweep, the second visual sweep, or a combination of the first and second visual sweeps. In other words, a sequence of two or more visual sweeps may be visually presented to the participant in succession. The two or more visual sweeps may be separated by a specified inter-stimulus-interval (ISI), which in some embodiments may be equal to the duration of each sweep. In other words, the presentation time (i.e., display time) of each of the sweeps may be equal to the ISI between the sweeps. Note, however, that in other embodiments, the ISI may not be equal to the sweep duration.

As one example, in cases where the at least two visual sweeps compose a sequence of two visual sweeps, visually presenting the at least two visual sweeps may include presenting a sequence of two visual sweeps comprising one of the following possible combinations: first visual sweep-first visual sweep, first visual sweep-second visual sweep, second visual sweep-first visual sweep, and second visual sweep-second visual sweep.

With respect to Task 1, where the visual sweeps comprise spatial frequency sweeps and where the frequency either increases or decreases, this increase/decrease of spatial frequency over time may be visually indicated by the bars of the pattern moving in/out, respectively. For example, increasing the frequency of a visual pattern increases the number of bars in a given area of the pattern, and so as the frequency is increased the bars may be seen to move inward towards the center of the pattern. Similarly, decreasing the frequency of a visual pattern decreases the number of bars in a given area of the pattern, and so as the frequency is decreased the bars may be seen to move outward away from the center of the pattern.

With respect to Task 2, where the visual sweeps comprise orientation sweeps in which the presented pattern rotates CCW or CW, the pattern, e.g., bars, will be seen to rotate through some specified angle.

The participant may then be required to indicate an order in which the at least two visual sweeps were presented, e.g., by providing input indicating the order. For example, in an embodiment where the visual sweeps are spatial frequency sweeps, if a sweep with increasing frequency is denoted by "IN", and a sweep with decreasing frequency is denoted by "OUT", then the possible orders for a two sweep sequence are IN-IN, IN-OUT, OUT-IN, and OUT-OUT. Thus, in the case of such a two-sweep sequence, the participant may be required to indicate one of these four orders. Note that in cases where the number of sweeps in a sequence is greater than two, the number of possible orders increases rapidly.

The participant preferably performs the exercise via a graphical user interface (GUI), using icons or buttons to indicate the order. Thus, in some embodiments, the method may include associating the first visual sweep with a first icon, and associating the second visual sweep with a second icon. For example, associating the first frequency sweep with the first icon may include visually presenting the first frequency sweep, and then highlighting the first icon to indicate to the participant the association, and similarly for the second sweep with a second icon. Both the first and second frequency sweeps are then available for visual presentation to the participant. Requiring the participant to indicate an order in which the at least two visual sweeps were presented may thus include requiring the participant to select the icons to indicate the order of the at least two visual sweeps.

A determination may then be made as to whether the participant indicated the order of the at least two visual sweeps correctly. In some embodiments, an indication, e.g., graphical and/or audible, may be provided to the participant indicating the correctness or incorrectness of the participant's response. For example, a "ding" or a "thunk" may be played to indicate correctness or incorrectness, respectively, and/or points may be awarded (in the case of a correct response). Of course, any other type of indication may be used as desired. The above visually presenting, requiring, and determining, may compose a trial in the exercise or task.

Thus, in an exemplary embodiment of a spatial frequency task with 2-sweep sequences, for a given trial, two visual sweeps, e.g., spatial frequency sweeps, may be presented briefly (e.g., for 27-1000 ms) separated by an ISI that may be equal to the presentation time. For 2-sweep sequences, there are four possible combinations of increasing or decreasing spatial frequency (increasing/increasing, decreasing/decreasing, increasing/decreasing, decreasing/increasing, which may be denoted by IN/IN, OUT/OUT, IN/OUT, and OUT/IN, as described above). As also described above, the participant's responses may be mouse clicks on icons indicating increasing or decreasing frequency of the bars, i.e., moving a cursor over the icon and clicking the mouse, although other indication means may be used as desired, e.g., arrow keys, etc. Thus, in this embodiment, the participant may give two responses per trial, corresponding to the two stimulus presentations, e.g., the two spatial frequency sweeps.

Similarly, in an exemplary embodiment of the orientation sweep task with 2-sweep sequences, for a given trial, two stimuli, specifically, two orientation sweeps, may be presented briefly (e.g., for 27-1000 ms) separated by a blank ISI (e.g., for 0-1500 ms). Again, for 2-sweep sequences, there are four possible combinations of rotations (CCW-CCW, CCW-CW, CW-CCW, and CW-CW). As noted above, responses may be mouse clicks on icons indicating clockwise rotation or counterclockwise rotation. Thus, in this embodiment, the participant may give two responses per trial, corresponding to the two stimulus presentations, e.g., the two orientation sweeps.

In preferred embodiments, the participant may perform the exercise or tasks via a graphical user interface (GUI). The GUI may include a stimulus presentation area where the visual sweeps may be presented to the participant, as well as means for receiving input from the participant. Additional GUI elements may also be provided for indicating various aspects of the participant's progress or status with respect to the exercise or task.

The visually presenting, requiring, and determining may be repeated one or more times in an iterative manner, to improve the participant's cognition, e.g., to improve the participant's ability to process visual information more quickly, read more efficiently, improve game performance, e.g., skiing, tennis, etc., and so forth. In other words, a plurality of trials may be performed in the exercise (preferably with respect to both tasks), where various orders of visual sweeps are presented to the participant, as described above. For example, the repetitions may be performed over a plurality of sessions, e.g., over days, weeks, or even months. In some embodiments, at the end of each session, the participant's score and thresholds for the session may be shown and may be compared to the best performance.

Such repeating preferably includes trials performed under a variety of specified stimulus conditions, e.g., with visual sweeps covering a range of sweep attributes. Such conditions may include baseline conditions, used before, after, and at specified points during, the exercise to assess the participant's performance, and non-baseline or training conditions, used for the actual training during the exercise. Thus, blocks of stimuli may contain particular conditions of base spatial frequency and orientation. As mentioned above, in some embodiments, the repeating may include performing trials in each of the visual sweep tasks described above, although in other embodiments, trials may only be performed in one visual sweep task, e.g., the frequency sweep task.

Each task may have a set of conditions specifying the visual sweeps for that task. For example, regarding the spatial frequency sweep task (Task 1), the conditions may specify one or more of: size of the sweep's image, rate or speed of the sweep, frequency range of the sweep, the colors of the sweep pattern, the orientation of the pattern, and/or the range of cycles/deg for the sweep, among others. Regarding the orientation sweep task (Task 2), the conditions may specify one or more of: the rate or speed of the sweep (i.e., rotation speed), the cycles/deg for the sweep pattern, size of the sweep's image, speed of the sweep, and/or the colors of the pattern, among others. However, it should be noted that other attributes may be used as desired.

In one embodiment, the repeating may include modifying or adjusting the stimulus intensity of the presented stimuli, e.g., the duration and/or ISI of the sweeps, or any other adjustable attribute of the stimulus or its presentation, based on the participant's response. Said another way, in each trial, and in response to the participant's indicated order of the visual sweeps, the stimulus intensity of the visual sweep may be adjusted for the next trial's visual presentation, i.e., based on whether the participant indicated the order of the at least two visual sweeps correctly (or not). The adjustments may generally be made to increase the difficulty of the stimulus when the participant answers correctly, and to decrease the difficulty of the stimulus when the participant answers incorrectly. Moreover, the adjustments may be made such that a specified level of performance, i.e., level of success, is approached and substantially maintained during performance of the exercise. For example, based on the participant's responses, the intensity of the visual sweeps may be adjusted to substantially achieve and maintain a specified success rate, e.g., 85% or 90%, for the participant, although other rates may be used as desired.

In preferred embodiments, the adjustments may be made using a maximum likelihood procedure, such as a QUEST (quick estimation by sequential testing) threshold procedure, or a ZEST (zippy estimation by sequential testing) threshold procedure, described below, such procedures being well-known in the art of stimulus threshold determination. In some embodiments, these adjustments (e.g., using ZEST) may be determined on a per condition basis. In other words, for each condition (used in each task), the visual sweeps may be presented (and adjusted) in accordance with a maximum likelihood procedure (e.g., ZEST) applied to trials under that condition.

Moreover, in some embodiments, the repeating may also include performing threshold assessments in conjunction with, or as part of, the exercise, e.g., using a 2-stair maximum likelihood procedure, such as a 2-stair ZEST procedure, e.g., at specific points during the exercise.

In some embodiments, the method may also include performing a plurality of "eureka" trials during the exercise. These trials may be performed periodically during the exercise, e.g., every 20 trials or so, where each eureka trial may comprise a non-Zest trial that is easier than the current threshold estimate—e.g. 2×threshold). In other words, the presentation time or duration may be twice that currently used in the exercise.

In some embodiments, the method may also include performing a plurality of practice trials, i.e., prior to performing the method elements described above. For example, in some embodiments, one or more practice sessions may be performed prior to the beginning of training to familiarize the participant with the nature and mechanisms of each task. For example, in one embodiment, before training begins for each of the spatial frequency and orientation tasks, the participant may perform at least one single sweep session, in which a single visual sweep is presented, and the participant is required to indicate the nature (e.g., direction) of the sweep, and at least one order task practice session, in which a sequence of visual sweeps are presented and the participant is required to indicate the order of the sweeps, as described above. In each practice session, a specified number of trials (e.g., 5) for each of one or more practice conditions may be performed, e.g., where each stimulus pattern is at 2 c/deg. In some embodiments, the participant may be able to invoke such practice sessions at will during the exercise, e.g., to re-familiarize the participant with the task at hand.

Other features and advantages of the present invention will become apparent upon study of the remaining portions of the specification and drawings.

DETAILED DESCRIPTION

Figure 1:
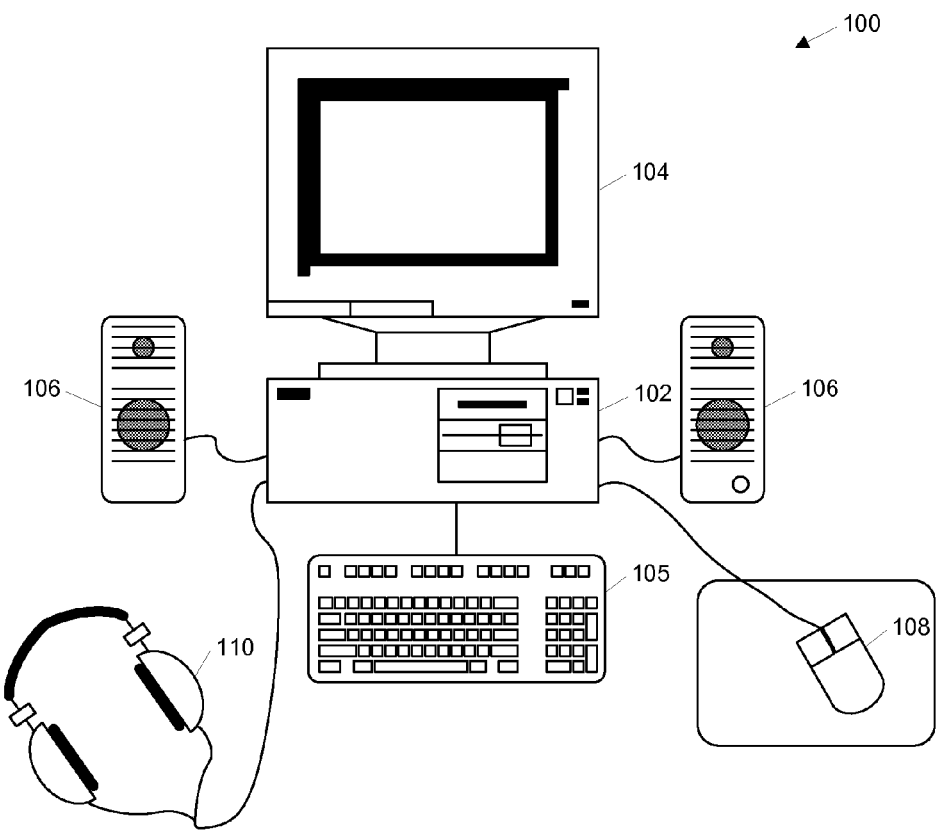
FIG. 1 is a block diagram of a computer system for executing a program according to some embodiments of the present invention.

Referring to FIG. 1, a computer system 100 is shown for executing a computer program to train, or retrain an individual according to the present invention to enhance cognition, where the term "cognition" refers to the speed, accuracy and reliability of processing of information, and attention and memory, and where the term "attention" refers to the facilitation of a target and/or suppression of a non-target over a given spatial extent, object-specific area or time window. The computer system 100 contains a computer 102, having a CPU, memory, hard disk and CD ROM drive (not shown), attached to a monitor 104. The monitor 104 provides visual prompting and feedback to the subject during execution of the computer program. Attached to the computer 102 are a keyboard 105, speakers 106, a mouse 108, and headphones 110. In some embodiments, the speakers 106 and the headphones 110 may provide auditory prompting and feedback to the subject during execution of the computer program. The mouse 108 allows the subject to navigate through the computer program, and to select particular responses after visual or auditory prompting by the computer program. The keyboard 105 allows an instructor to enter alphanumeric information about the subject into the computer 102. Although a number of different computer platforms are applicable to the present invention, embodiments of the present invention execute on either IBM compatible computers or Macintosh computers, or similarly configured computing devices such as set top boxes, PDA's, gaming consoles, etc.

Figure 2:
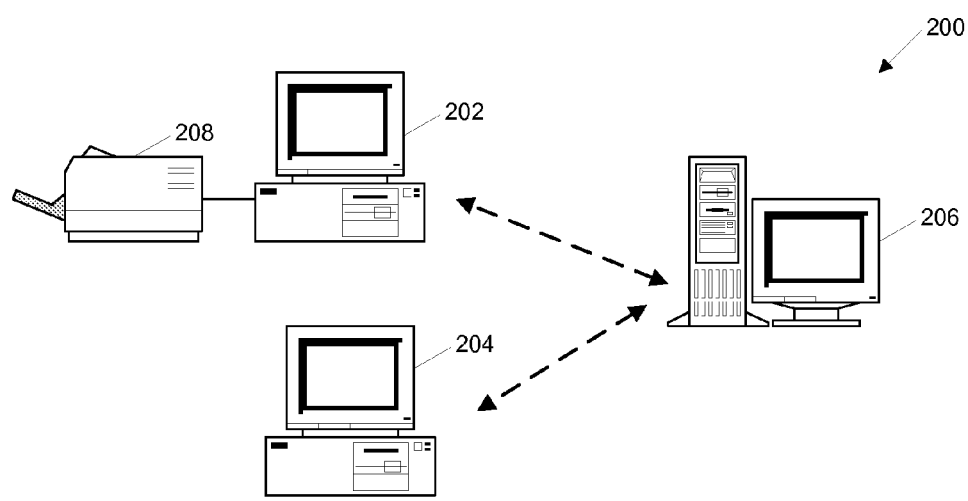
FIG. 2 is a block diagram of a computer network for executing a program according to some embodiments of the present invention.

Now referring to FIG. 2, a computer network 200 is shown. The computer network 200 contains computers 202, 204, similar to that described above with reference to FIG. 1, connected to a server 206. The connection between the computers 202, 204 and the server 206 can be made via a local area network (LAN), a wide area network (WAN), or via modem connections, directly or through the Internet. A printer 208 is shown connected to the computer 202 to illustrate that a subject can print out reports associated with the computer program of the present invention. The computer network 200 allows information such as test scores, game statistics, and other subject information to flow from a subject's computer 202, 204 to a server 206. An administrator can review the information and can then download configuration and control information pertaining to a particular subject, back to the subject's computer 202, 204.

Embodiments of the computer-based exercises or tasks described herein may operate to renormalize and improve the ability of the visual nervous system to accurately encode information about multiple visual events of short duration. This may be achieved by having participants perform a time order judgment task under conditions of high engagement/stimulation and under high reward for correct performance in order to encourage renormalization of visual spatiotemporal representations. The design of these exercises is tailored to drive responses in a large proportion of neurons in the early visual cortex (e.g, areas V1, V2, V3, V4, MT, etc.) successively, while forcing neurons at a higher level of sensory processing to extract temporal information about the order in which particular neurons fired.

Visual Sweep Exercise

Below are described various embodiments of a cognitive training exercise that utilizes visual sweeps, e.g., of spatial frequency and/or orientation patterns, to improve cognition of a participant, e.g., an aging adult. Two exemplary tasks using such visual sweeps are first described, after which the general exercise is described. It should be noted that various embodiments of the visual sweep tasks described herein, or other visual sweep tasks, may be used singly or in combination in the exercise. Moreover, as described below, in some embodiments, stimulus threshold assessments may also be performed in conjunction with, or as part of, the exercise, thus facilitating more effective training of the participant's cognitive system.

Note that in preferred embodiments, the exercise may be presented in the context of a game (or games). In other words, the visual sweep exercise(s) described herein may be implemented, embedded, or encapsulated, in a game, where the game elements, although not necessarily related to the particular task(s) of the exercise (e.g., the visual sweeps), may provide mechanisms for engaging the participant, and keeping the participant engaged and interested in progressing through the exercise, e.g., by providing a reward structure, progress cues, and so forth. Examples of such games are described below.

Visual Sweep Tasks

The two tasks described below visually present spatial frequency patterns to a participant, and receive input from the participant in response that characterizes the patterns in some way, such as the direction of a frequency sweep (Task 1) or a changing orientation of the pattern (Task 2), although in other embodiments, other visual sweep tasks may also be utilized. Difficulty on these tasks may be manipulated by adjusting the durations of the stimulus presentations/ISI, as will be described in detail below. These tasks may be performed singly or in combination in the visual sweep exercise, described below.

Task 1: Spatial Frequency Sweep Time Order Judgment

In this task, the participant may perform a time order judgment task in which he or she is required to indicate for each of two time intervals whether a presented spatial frequency pattern was expanding or contracting in spatial frequency. Spatial frequency is a characteristic of how a pattern repeats itself over space. For a pattern made up of bars, the wider the bars, the lower the spatial frequency. A sweep of spatial frequency in the visual domain is analogous to an FM (frequency modulation) sweep in the auditory domain. One of the most salient features of the response properties of neurons in the early visual cortex (e.g., V1, V2, etc.) is their selectivity for the spatial frequency of periodic patterns. Some neurons are tuned to higher spatial frequencies (thin bars), while other neurons are tuned to lower spatial frequencies (thick bars). By sweeping in spatial frequency, many more neurons may be stimulated on a given trial than is possible by presenting a single frequency. Additionally, in this task, the same neurons may be stimulated in both presentation intervals whether patterns are sweeping toward higher or lower spatial frequencies. By engaging the participant repetitively in such an identification task, more precise and temporally segregated representations of spatial frequency and change in spatial frequency in the visual cortex may be facilitated. The ability to encode such information is critical for accurately representing objects that are moving relative to an observer (e.g., the world as the observer moves through it).

In a preferred embodiment, stimuli for the task may be sine wave modulated gratings that change in spatial frequency over time, although in other embodiments, other frequency patterns may be used as desired, e.g., concentric circles, stark black and white bars, etc. A sine wave modulated grating is a pattern that varies in luminance (roughly equivalent to the phenomenal experience of lightness) as a sine function of space along a particular dimension. A horizontal sine wave grating varies in luminance as a function of the y-dimension of space. A vertical sine wave grating varies in luminance as a function of the x-dimension of space. It should be noted that sine wave gratings can appear at any orientation.

Figure 3:
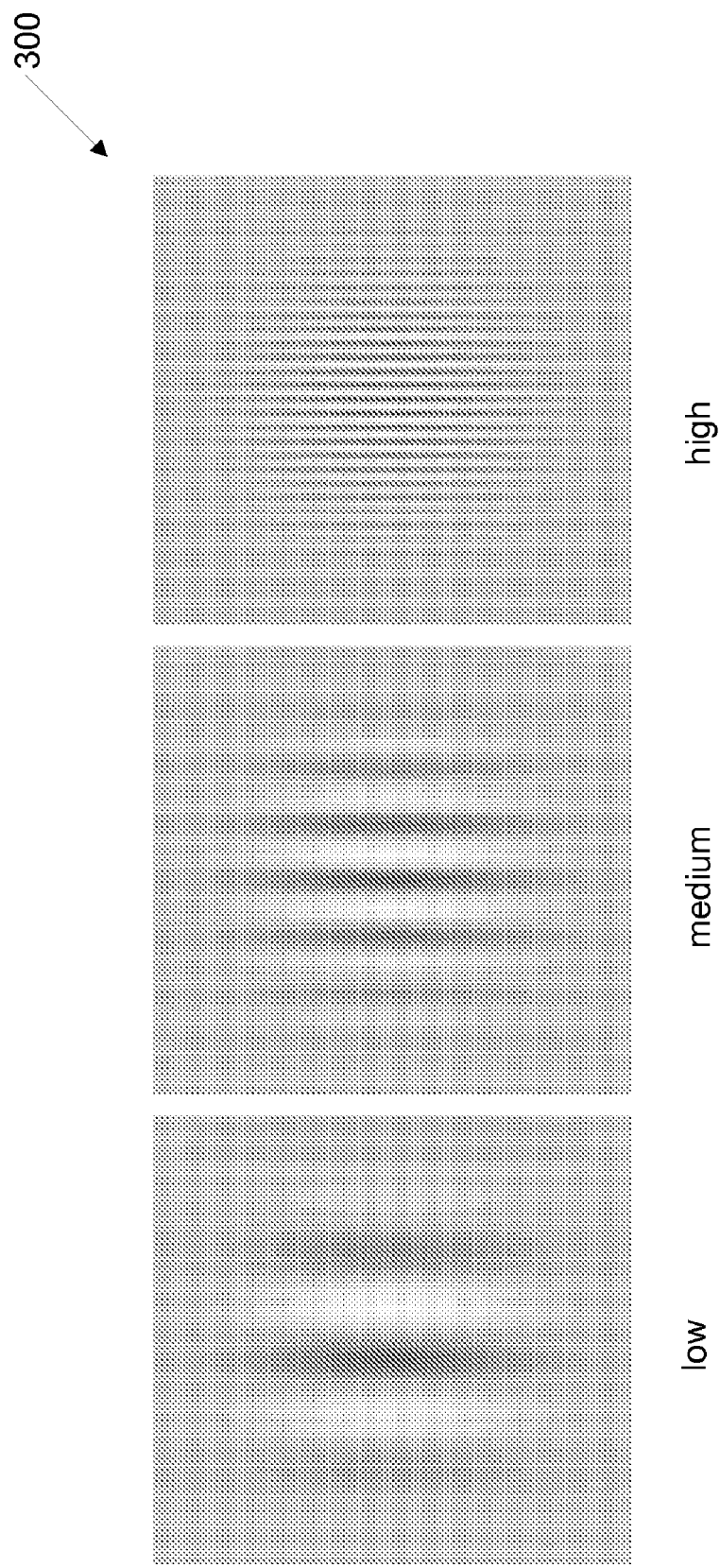
FIG. 3 illustrates examples of Gabor gratings at different spatial frequencies, according to one embodiment.

The gratings may be windowed by a 2-dimensional Gaussian to remove sharp edges which otherwise introduce high spatial frequency intrusions. This windowed pattern is referred to as a Gabor stimulus. The frequency of the modulation over space (the spatial frequency) is inversely related to the distance between the luminance peaks (the white stripes), i.e., the "wavelength" of the pattern. FIG. 3 illustrates examples of Gabor gratings 300 at different spatial frequencies. As may be seen, FIG. 3 includes examples of low, medium and high spatial frequency vertically oriented Gabor gratings. Note that due to the Gaussian windowing, each image becomes fainter toward the edges of the image.

The frequency of each Gabor pattern may be represented in cycles (wavelengths) per degree, e.g., c/deg, where the determination of spatial frequency in cycles per degree depends on the distance of the observer from the screen (one exemplary distance value for this purpose used herein is 51 cm, although it should be noted that other distance values may be used as desired, e.g., 57 cm). In one embodiment, the color of the presented patterns may vary pseudo-randomly from trial to trial among colors that map to distinct points in a physiologically motivated chromaticity space (cone contrast space). The colors correspond to +S (increment from white for S cones), −S (decrement from white for S cones), +L/−M (increment for L cones and decrement for M cones), and L/+M (decrement for L cones, increment for M cones), although other color schemes may be used as desired.

Note that the maximum c/deg that can be adequately rendered on a monitor depends on the spatial resolution of the monitor and the viewing distance. A far viewing distance is best for the Visual Sweep exercises because higher spatial frequency patterns (thinner bars) may be presented. A close viewing distance is better for Eye Movement exercises because the target stimuli can be placed further out in peripheral vision.

Figure 4A:
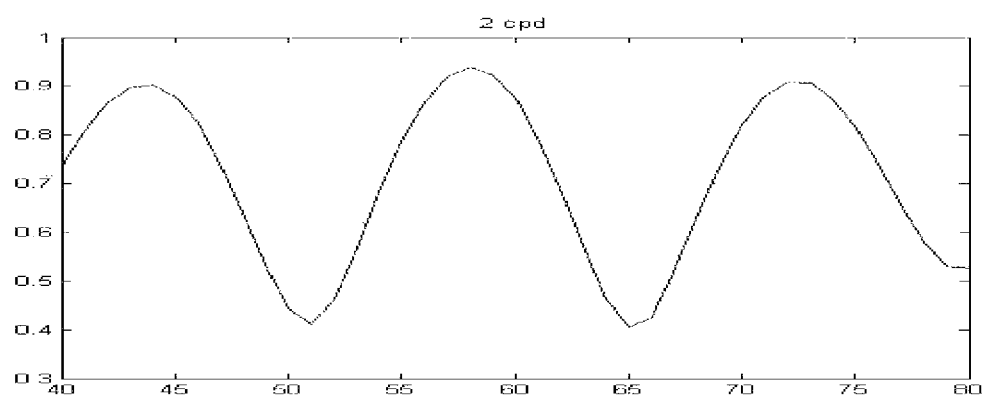
FIGS. 4A and 4B illustrate cross sectional profiles of various Gabor stimuli.
Figure 4A:
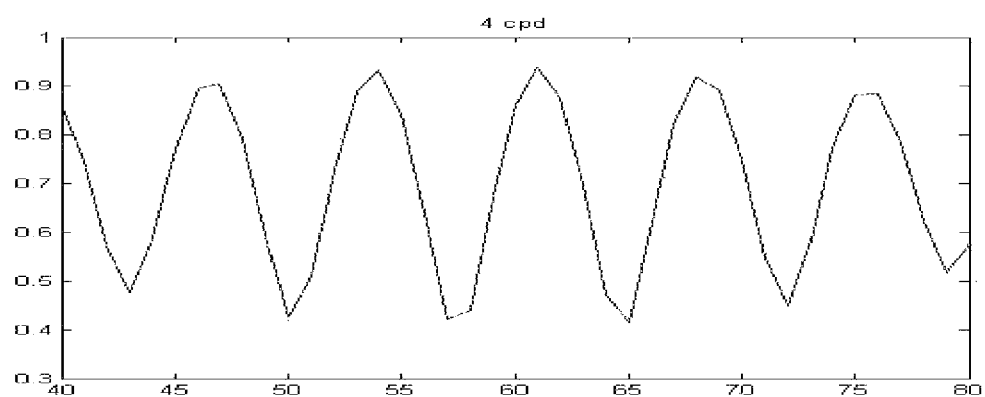
Figure 4A:
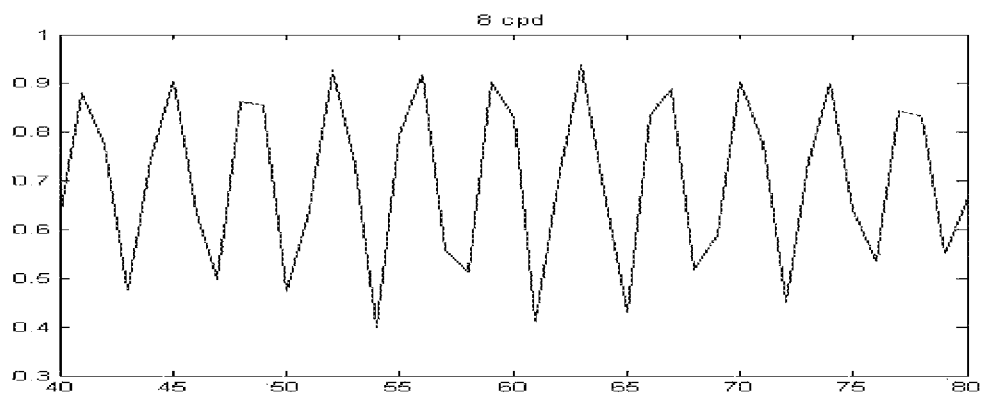
Figure 4B:
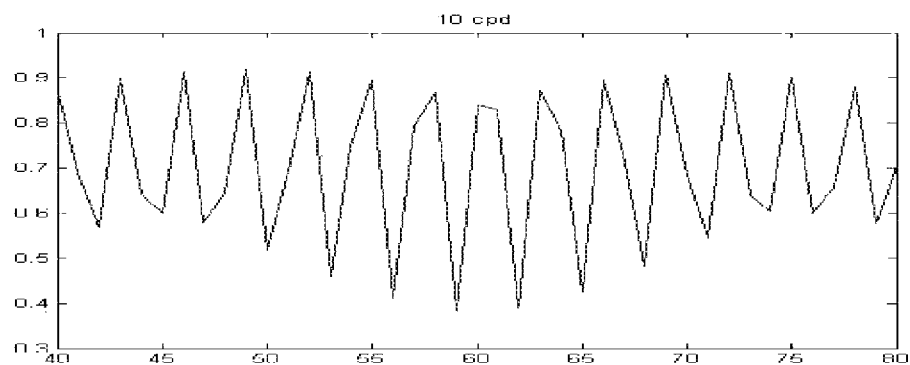
Figure 4B:
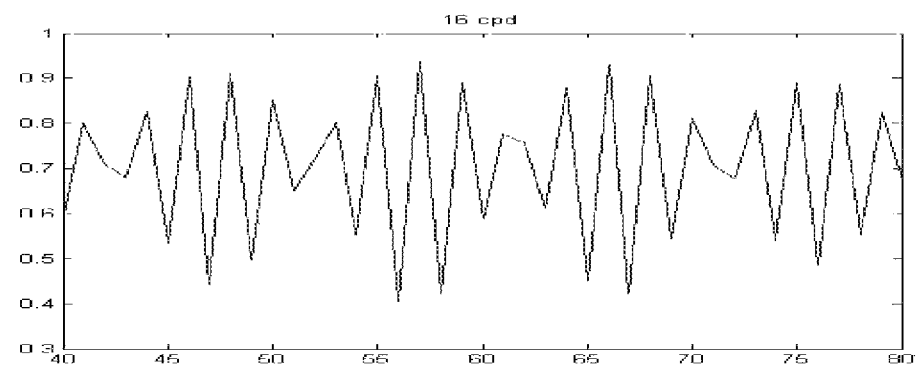
Figure 5:
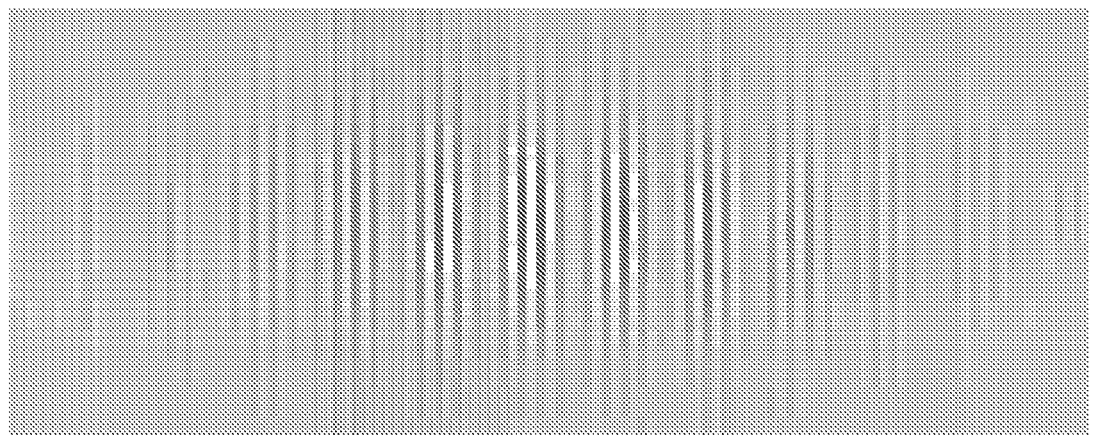
FIG. 5 illustrates aliasing in a spatial frequency pattern.

For example, FIGS. 4A and 4B illustrate cross sectional profiles of Gabor stimuli when rendered on a computer monitor at an exemplary spatial resolution of 800×600 and an exemplary viewing distance of 51 cm. As labeled, the profiles are presented for 2, 4, 8 (FIG. 4A), 10 and 16 (FIG. 4B) c/deg. Note that, as the profiles of FIG. 4B show, at about 10 c/deg and above, aliasing may produce secondary spatial frequencies, represented in the profiles as envelopes modulating the amplitudes of the signals. This aliasing is also apparent in the spatial frequency pattern of FIG. 5. Note the secondary periodicity overlaid or superimposed on the light/dark bars, wherein the dark bars lighten and darken in a periodic manner in the horizontal direction.

The maximum c/deg (also referred to as cpd) that can be adequately rendered may be about 5 c/deg. At closer viewing distances and lower spatial resolutions, the profiles will typically deteriorate further. Thus, in preferred embodiments, test patterns between 0.5 c/deg and 5 c/deg may be used. Note that a single sweep of 0.5 to 5 c/deg is generally too easy for the participant and thus may generally be broken down into smaller ranges for training purposes. For example, in some embodiments, 3 ranges may be used for training purposes: a low range of 0.5 to 1.26 c/deg, a medium range of 1.26 to 3.18 c/deg, and a high range of 3.18 to 5 c/deg, although it should be noted that these ranges are intended to be exemplary only, and that other ranges (and numbers of ranges) may be used as desired. In some embodiments, for 17" monitors, a view distance of approximately 20.0 inches may be desired, and for 19" monitors, a view distance of approximately 22.5 inches may be desired.

In some embodiments, during the course of the task, patterns may be presented at various orientations, e.g., at 4 orientations: 90 deg (vertical), 0 deg (horizontal), 45 deg (diagonal 1), and 135 deg (diagonal 2), although other orientations may be used as desired (although this should not be confused with Task 2, described below). The contrast of the gratings may be set at 75%, e.g., using the well-known Michelson calculation method. Additionally, the pixels values may be gamma corrected, e.g., using a gamma value of 2.2.

Task 2: Orientation Sweep Time Order Judgment

In this task, the participant may perform a time order judgment task in which he or she may be required to indicate for each of two or more orientation sweeps whether the pattern was rotating clockwise or counterclockwise. In other words, two or more spatial frequency patterns may be presented in succession, where during each presentation, the pattern is rotated at a specified rate through a specified angle, after which the participant may be required to indicate, in order, the rotation direction of each pattern, e.g., clockwise (CW) or counter-clockwise (CCW).

One salient characteristic of the tuning properties of the neurons in the areas of the early visual cortex (e.g, V1, V2, etc.) is their selectivity for the orientation of elongated, periodic patterns. Neurons in these areas (and several other primarily visual areas) will respond selectively to patterns in their receptive fields at their preferred orientation, and are increasingly less likely to respond to patterns at increasingly different orientations. Most neurons in early visual areas will not respond to patterns that presented in their receptive fields at an orientation that is orthogonal (perpendicular) to their preferred orientation. By sweeping these patterns in orientation (i.e., rotating them), many more neurons may be stimulated on a given trial than is possible by presenting a single orientation. Additionally, the same neurons may be stimulated in both presentation intervals whether the patterns are sweeping clockwise or counterclockwise. By engaging participants repetitively in such an identification task, more precise and temporally segregated representations of orientation and change in orientation in the visual cortex may be facilitated. Precise representations of orientation are critical to accurately encoding all spatial information as well as processing motion information, especially regarding self motion—particularly as it pertains to posture.

In a preferred embodiment, stimuli for this task may be Gabor patterns that change in orientation over time (see Task 1 discussion above for a description of Gabor patterns), although, as with the spatial frequency sweep task described above, in other embodiments, other patterns may be used as desired. Orientations may be specified in terms of degrees (0-360°), although other units, such as radians, may be used as desired. An orientation of 0° may represent a horizontal pattern, while 90° may correspond to a vertical pattern.

Figure 6:
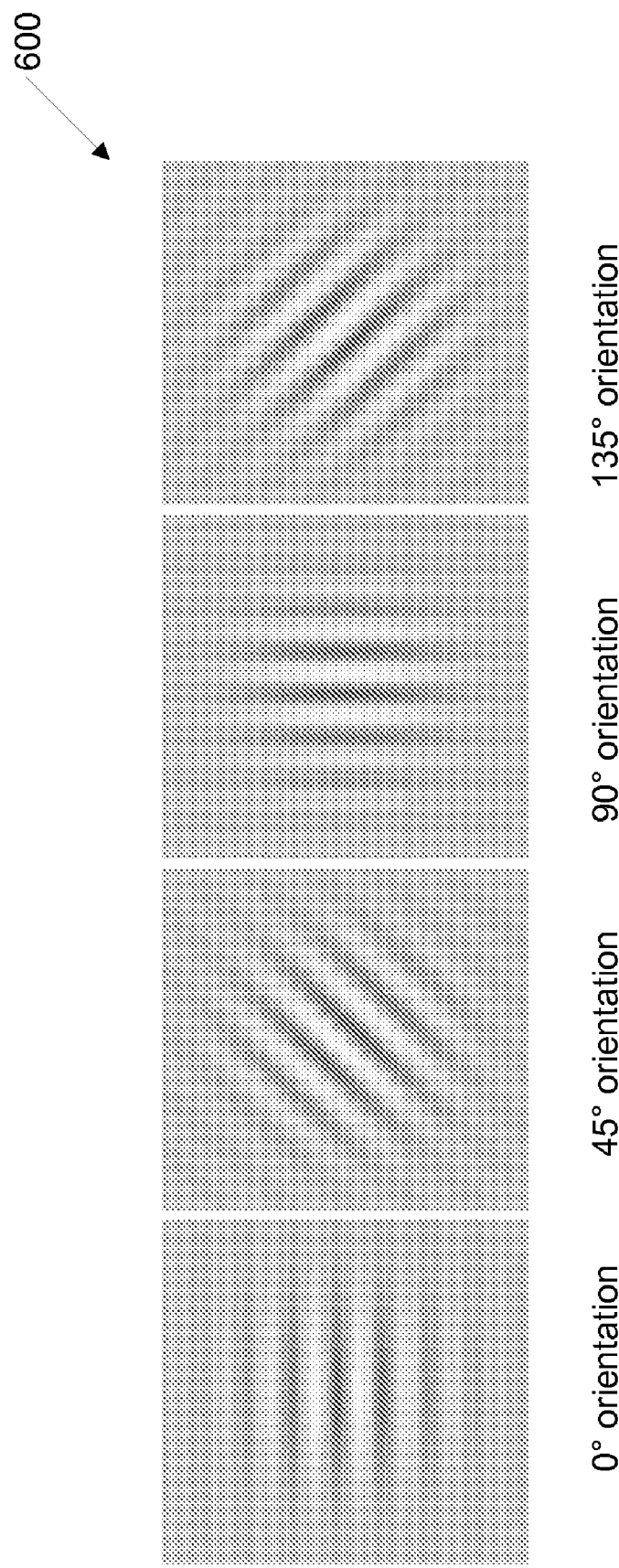
FIG. 6 illustrates exemplary Gabor patterns at various orientations, according to one embodiment.

FIG. 6 illustrates exemplary Gabor patterns at various orientations, specifically, at 0, 45, 90, and 135 degrees, respectively. In this orientation sweep task, patterns may be presented at a specified number of speeds of rotation, e.g., 3 different speeds, and at a specified number of spatial frequencies, e.g., 4 different spatial frequencies. In one embodiment, the speeds of rotation may be 180°, 360°, or 720°/sec, although other values may be used as desired. Spatial frequencies may include 0.5, 1, 2 and 4 c/deg, although other values may be used as desired. The initial orientation and color of the pattern may vary randomly from trial to trial. In one embodiment, the maximum sweep may be 45 degrees, although other values may be used as desired.

Figure 7:
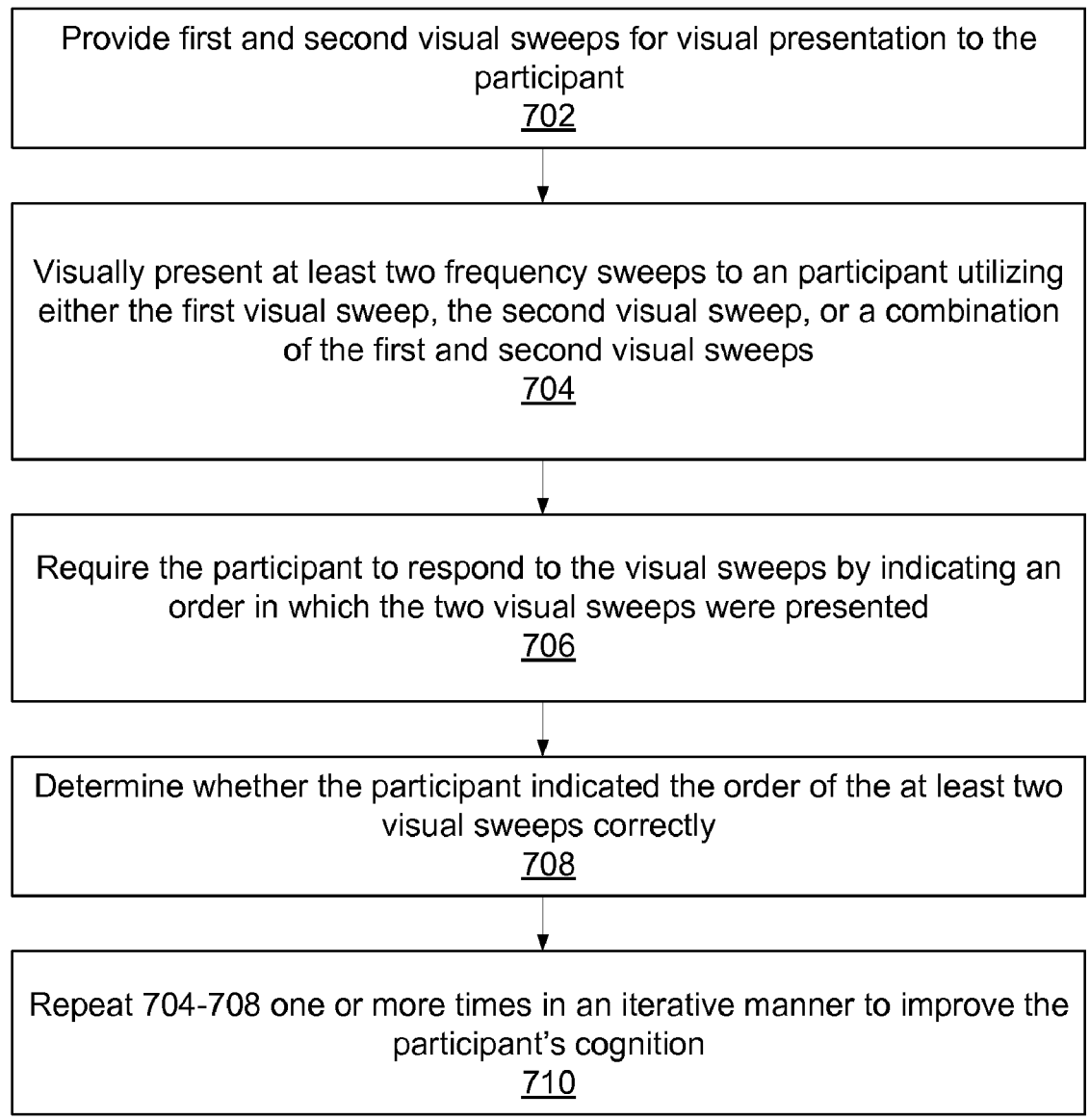
FIG. 7 is a high-level flowchart of one embodiment of a method for cognitive training using visual sweeps, according to one embodiment.

FIG. 7—Flowchart of a Method for Cognitive Training Using Visual Sweeps

FIG. 7 is a high-level flowchart of one embodiment of a method for cognitive training using visual sweeps. More specifically, the method utilizes a computing device to present visual sweeps, such as, for example, spatial frequency and/or orientation sweeps, for training, and to record responses from the participant. It should be noted that in various embodiments, some of the method elements may be performed concurrently, in a different order than shown, or may be omitted. Additional method elements may also be performed as desired. As shown, the method may be performed as follows:

In 702, first and second visual sweeps may be provided, where both the first and second spatial frequency sweeps are available for visual presentation to the participant. For example, the first and second visual sweeps may be spatial frequency sweeps, or orientation sweeps, although other types of visual sweeps may also be used as desired.

In 704, at least two visual sweeps may be visually presented to the participant utilizing either the first visual sweep, the second visual sweep, or a combination of the first and second visual sweeps. In other words, a sequence of two or more visual sweeps may be visually presented to the participant in succession. The two or more visual sweeps may be separated by a specified inter-stimulus-interval (ISI), which in some embodiments may be equal to the duration of each sweep. In other words, the presentation time (i.e., display time) of each of the sweeps may be equal to the ISI between the sweeps. Note, however, that in other embodiments, the ISI may not be equal to the sweep duration.

As one example, in cases where the at least two visual sweeps compose a sequence of two visual sweeps, visually presenting the at least two visual sweeps may include presenting a sequence of two visual sweeps comprising one of the following possible combinations: first visual sweep-first visual sweep, first visual sweep-second visual sweep, second visual sweep-first visual sweep, and second visual sweep-second visual sweep.

With respect to Task 1, where the visual sweeps comprise spatial frequency sweeps and where the frequency either increases or decreases, this increase/decrease of spatial frequency over time may be visually indicated by the bars of the pattern moving in/out, respectively. For example, increasing the frequency of a visual pattern increases the number of bars in a given area of the pattern, and so as the frequency is increased the bars may be seen to move inward towards the center of the pattern. Similarly, decreasing the frequency of a visual pattern decreases the number of bars in a given area of the pattern, and so as the frequency is decreased the bars may be seen to move outward away from the center of the pattern. Examples of Gabor patterns with various frequencies are illustrated in FIG. 3. Note that in some cases the monitor refresh rate may restrict the range of c/deg that can be presented within a certain time. Once the threshold has dropped below a certain number of frames (e.g. 10 frames, or 133 ms at 75 Hz), the c/deg range may be reduced by an equal amount at each end of the range extremes, e.g., using a log 10 scale.

With respect to Task 2, where the visual sweeps comprise orientation sweeps in which the presented pattern rotates CCW or CW, the pattern, e.g., bars, will be seen to rotate through some specified angle. Examples of Gabor patterns at various orientations are illustrated in FIG. 6, specifically, at 0, 45, 90, and 135 degrees.

In 706, the participant may be required to indicate an order in which the at least two visual sweeps were presented, e.g., by providing input indicating the order.

For example, in an embodiment where the visual sweeps are spatial frequency sweeps, if a sweep with increasing frequency is denoted by "IN", and a sweep with decreasing frequency is denoted by "OUT", then the possible orders for a two sweep sequence are IN-IN, IN-OUT, OUT-IN, and OUT-OUT. Thus, in the case of such a two-sweep sequence, the participant may be required to indicate one of these four orders. Note that in cases where the number of sweeps in a sequence is greater than two, the number of possible orders increases rapidly.

As will be described below in more detail, the participant preferably performs the exercise via a graphical user interface (GUI), using icons or buttons to indicate the order. Thus, in some embodiments, the method may include associating the first visual sweep (of 702) with a first icon, and associating the second visual sweep (of 702) with a second icon. For example, associating the first frequency sweep with the first icon may include visually presenting the first frequency sweep, and then highlighting the first icon to indicate to the participant the association. Similarly, associating the second frequency sweep with the second icon may include visually presenting the second frequency sweep, and then highlighting the second icon to indicate to the participant the association. Both the first and second frequency sweeps are then available for visual presentation to the participant. Requiring the participant to indicate an order in which the at least two visual sweeps were presented may thus include requiring the participant to select the icons to indicate the order of the at least two visual sweeps.

In 708, a determination may be made as to whether the participant indicated the order of the at least two visual sweeps correctly. In some embodiments, an indication, e.g., a graphical or audible indication, may be provided to the participant indicating the correctness or incorrectness of the participant's response. For example, a "ding" or a "thunk" may be played to indicate correctness or incorrectness, respectively, and/or points may be awarded (in the case of a correct response). Of course, any other type of indication may be used as desired. The above visually presenting, requiring, and determining, may compose a trial in the exercise or task.

Thus, in an exemplary embodiment of a spatial frequency task with 2-sweep sequences, for a given trial, two visual sweeps, e.g., spatial frequency sweeps, may be presented briefly (e.g., for 27-1000 ms) separated by an ISI that may be equal to the presentation time. For 2-sweep sequences, there are four possible combinations of increasing or decreasing spatial frequency (increasing/increasing, decreasing/decreasing, increasing/decreasing, decreasing/increasing, which may be denoted by IN/IN, OUT/OUT, IN/OUT, and OUT/IN, as described above). As also described above, the participant's responses may be mouse clicks on icons indicating increasing or decreasing frequency of the bars, i.e., moving a cursor over the icon and clicking the mouse, although other indication means may be used as desired, e.g., arrow keys, etc. Thus, in this embodiment, the participant may give two responses per trial, corresponding to the two stimulus presentations, e.g., the two spatial frequency sweeps.

Similarly, in an exemplary embodiment of the orientation sweep task with 2-sweep sequences, for a given trial, two stimuli, specifically, two orientation sweeps, may be presented briefly (e.g., for 27-1000 ms) separated by a blank ISI (e.g., for 0-1500 ms). Again, for 2-sweep sequences, there are four possible combinations of rotations (CCW-CCW, CCW-CW, CW-CCW, and CW-CW). As noted above, responses may be mouse clicks on icons indicating clockwise rotation or counterclockwise rotation. Thus, in this embodiment, the participant may give two responses per trial, corresponding to the two stimulus presentations, e.g., the two orientation sweeps.

In preferred embodiments, the participant may perform the exercise or tasks via a graphical user interface (GUI). The GUI may include a stimulus presentation area where the visual sweeps of 704 may be presented to the participant, as well as means for receiving input from the participant. As will be described below with respect to particular task GUIs, additional GUI elements may be provided for indicating various aspects of the participant's progress or status with respect to the exercise or task.

Figure 8:
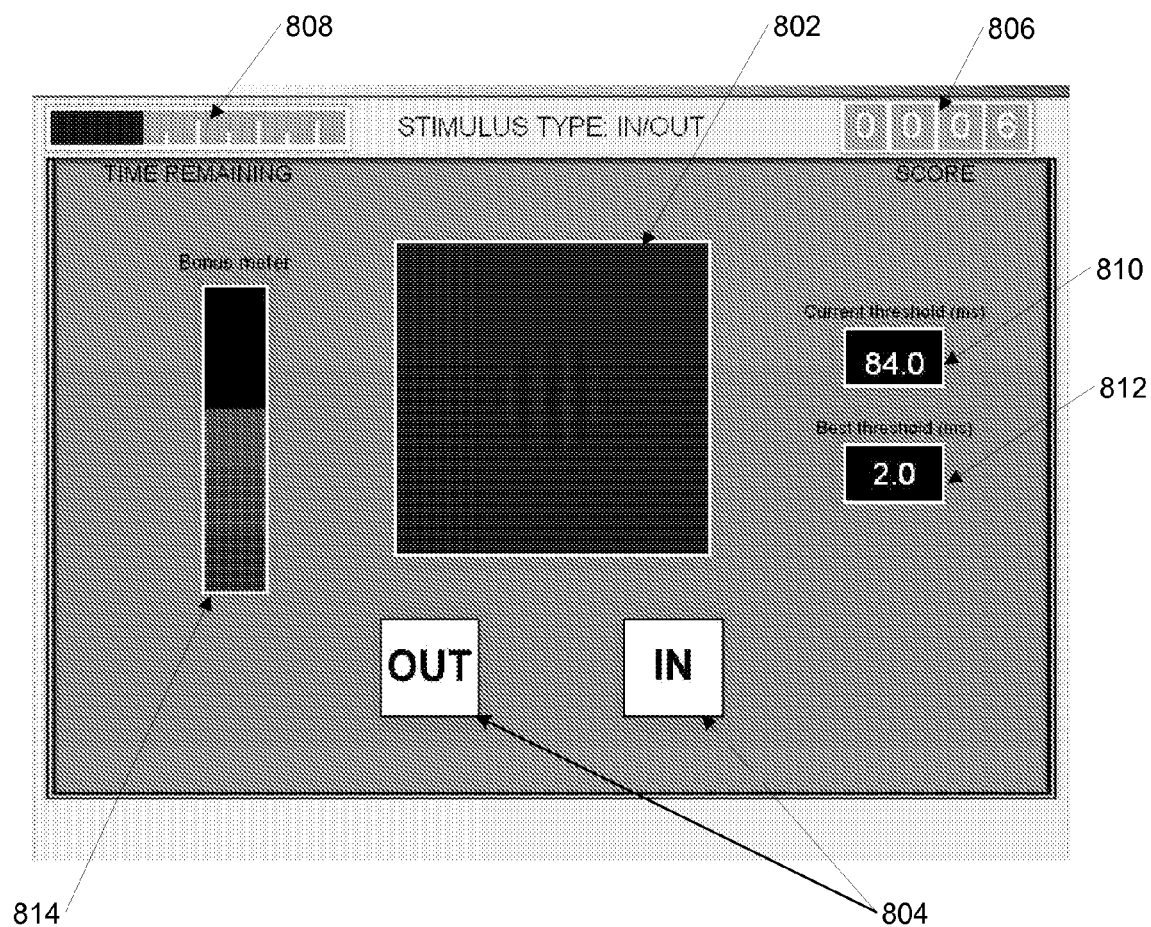
FIG. 8 illustrates an exemplary simple GUI suitable for implementing various embodiments of a spatial frequency sweep exercise, according to one embodiment.

FIG. 8 illustrates an exemplary simple GUI suitable for implementing various embodiments of the present invention, specifically, embodiments of Task 1 (spatial frequency sweep). As FIG. 8 shows, the GUI includes a stimulus presentation area 802 where the visual sweeps of 704, in this case, spatial frequency sweeps, may be presented to the participant. The GUI may also include means for receiving input from the participant. For example, in the example GUI of FIG. 8, icons 804, e.g., buttons labeled "IN" and "OUT", respectively, may be provided whereby the participant may indicate the nature of each sweep. For example, in the case of a sweep sequence IN-OUT, after the two sweeps have been presented (704), the participant may select an icon or button for each of the sweeps, thus, the participant may select the IN icon, then the OUT icon, to indicate the order (and character) of the sweeps. As noted above, in some embodiments, sequences with greater than two sweeps may also be used. As FIG. 8 also shows, in this embodiment, a score indicator 806 may be displayed in the GUI that indicates the participant's current score in the task or exercise. The GUI may also include a time remaining indicator 808 that provides an indication of how much time remains in the current task, session, or exercise. As also shown, the GUI may present threshold information, such as the current threshold value 810, and a best threshold value 812, where a threshold indicates the value of an adjustable stimulus attribute or adaptive dimension, referred to as the stimulus intensity, that results in a specified performance level, i.e., success rate, for the participant, one example being the duration or presentation time of a sweep, as will be explained below in more detail. In various embodiments, the GUI may also include additional indicators, such as, for example, a bonus meter (or equivalent) 814, which may indicate the number of correct responses in a row, and may flash, play music, and/or award bonus points, when some specified number, e.g., 5, in a row is attained.

Figure 9:
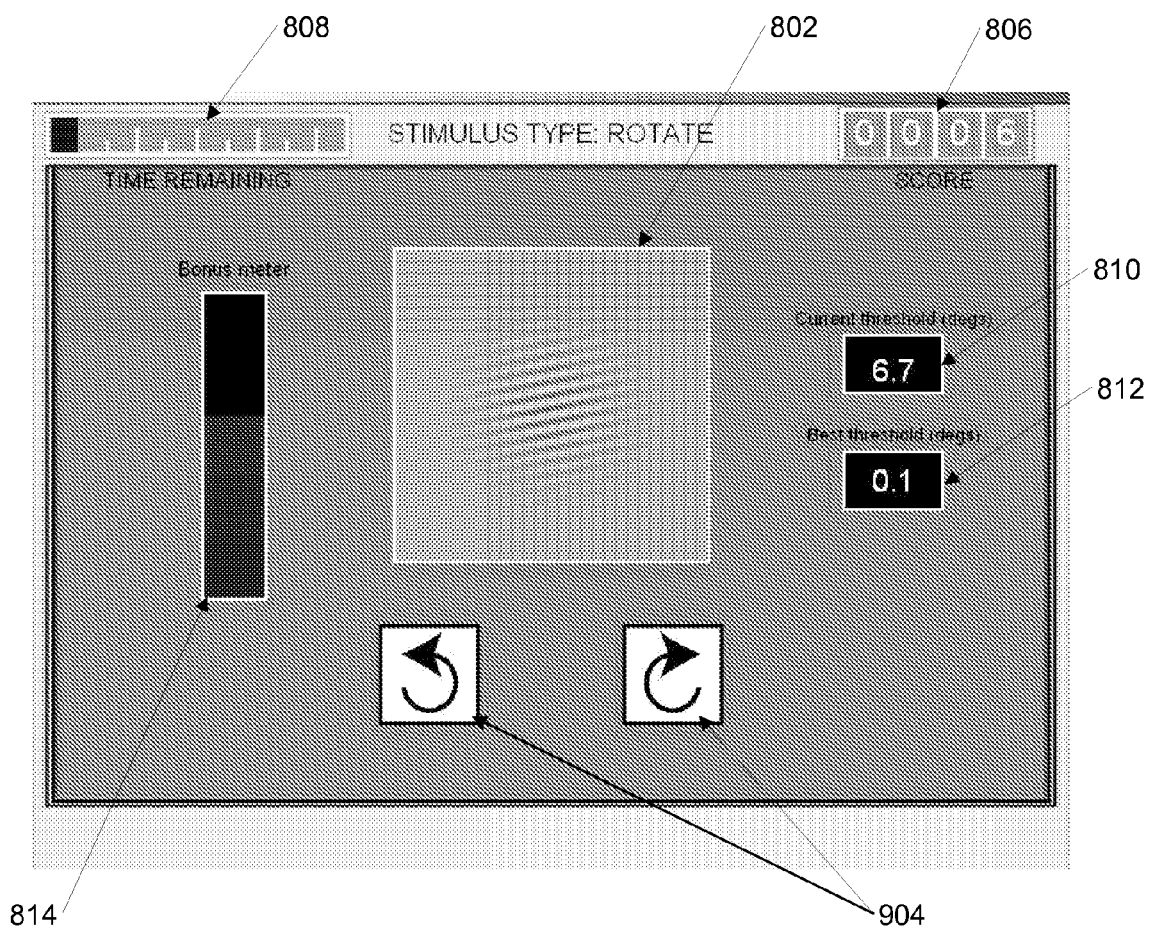
FIG. 9 illustrates an exemplary simple GUI suitable for implementing various embodiments of an orientation sweep exercise, according to one embodiment.

FIG. 9 illustrates an exemplary simple GUI suitable for implementing various embodiments of Task 2 (orientation sweep). As may be seen, this exemplary GUI is similar to that of FIG. 8, but with these differences: the stimulus presentation area 802 is used to present orientation sweeps to the participant, and rather than icons 804, e.g., buttons labeled "IN" and "OUT", the icons or buttons indicate counter-clockwise and clockwise, respectively, corresponding to the possible directions of the pattern rotation (orientation sweep). Thus, for example, in the case of a sweep sequence CCW-CW, after the two sweeps have been presented (704), the participant may select an icon or button for each of the sweeps, e.g., the CCW icon, then the CW icon, to indicate the order (and character) of the sweeps. It should be noted that the GUIs of FIGS. 8 and 9 are meant to be exemplary only, and that other GUIs are envisioned, as will be presented further below.

Thus, in one embodiment, the requiring of 706 may include receiving input from the participant selecting the icons in an order that indicates the order in which the at least two frequency sweeps were presented. Selection of the icons may be made by the participant placing a cursor over an icon and clicking a mouse, where each mouse click is recorded as a selection. The selections made by the participant may be recorded. Additionally, whether in 708 the participant correctly identified the order in which the at least two frequency sweeps were presented may also be recorded.

In 710, the visually presenting, requiring, and determining of 704, 706, and 708 may be repeated one or more times in an iterative manner, to improve the participant's cognition, e.g., to improve the participant's ability to process visual information more quickly, read more efficiently, improve game performance, e.g., skiing, tennis, etc., and so forth. In other words, a plurality of trials may be performed in the exercise (preferably with respect to both tasks), where various orders of visual sweeps are presented to the participant, as described above. For example, the repetitions may be performed over a plurality of sessions, e.g., over days, weeks, or even months. In some embodiments, at the end of each session, the participant's score and thresholds for the session may be shown and may be compared to the best performance.

Such repeating preferably includes trials performed under a variety of specified stimulus conditions, e.g., with visual sweeps covering a range of sweep attributes. Such conditions may include baseline conditions, used before, after, and at specified points during, the exercise to assess the participant's performance (described further below), and non-baseline or training conditions, used for the actual training during the exercise. Thus, blocks of stimuli may contain particular conditions of base spatial frequency and orientation. As mentioned above, in preferred embodiments, the repeating may include performing trials in each of the visual sweep tasks described above.

Each task may have a set of conditions specifying the visual sweeps for that task. For example, regarding the spatial frequency sweep task (Task 1), the conditions may specify one or more of: size of the sweep's image, rate or speed of the sweep, frequency range of the sweep, the colors of the sweep pattern, the orientation of the pattern, and/or the range of cycles/deg for the sweep. Regarding the orientation sweep task (Task 2), the conditions may specify one or more of: the rate or speed of the sweep (i.e., rotation speed), the cycles/deg for the sweep pattern, size of the sweep's image, speed of the sweep, and/or the colors of the pattern. However, it should be noted that other attributes may be used as desired.

There are a variety of ways that the visual sweep tasks may be performed over the course of the exercise. For example, in one exemplary training schedule or regimen, on first alternate sessions, trials under a first number of conditions may be performed for the spatial frequency sweep task, and under a second number of conditions for the orientation sweep task, and on second alternate sessions, trials under the second number of conditions may be performed for the spatial frequency sweep task, and under the first number of conditions for the orientation sweep task, where the first alternate sessions and the second alternate sessions are interleaved, e.g., the respective number of conditions used per task may alternate on a per session basis. Thus, in an embodiment where the repeating is performed over a 48 day training period, and where the participant is trained on 2 conditions per day (e.g., for a total of 10 minutes), of the two conditions, 1 may be from one sweep type, and 1 may be from the other sweep type, and this may alternate with each training session.

In another exemplary schedule, the type of sweep may be consistent for that day (either spatial frequency sweeps or orientation sweeps) and may alternate each day. In other words, on a particular day, the participant may be presented trials under two conditions for one type of sweep only (either spatial frequency or orientation). The next day, the participant may be presented with trials under conditions for the other type of sweep. Thus, for example, a block sequence may be trained on every other day for a total of 5 days. This approach may maximize the training effect of the exercise.

In one embodiment, the participant may train on each condition 5 times, and may take 10 days to finish each of a number of stimulus blocks (e.g., 4) over the 48 day training period, which may minimize uncertainty and maximize the training effect of the exercise. Thus, in these embodiments, there may be a total of 8 hours training (on this exercise) spread over 48 training sessions (e.g., at 10 minutes per session).

In another exemplary training regimen, there may be a total of 8 hours of play, where each session is 10 minutes long, with approximately two configurations played per session.

It should be noted that the above training schedules or regimens are meant to be exemplary only, and are not intended to limit the training schedule or regimen used to any particular approach. Thus, in preferred embodiments, the exercise may include performing multiple tasks, e.g., Task 1 and Task 2, using frequency patterns.

Exemplary conditions, including baseline (assessment) and non-baseline (training) conditions, are provided below.

In one embodiment, the repeating may include modifying or adjusting the stimulus intensity of the presented stimuli, e.g., the duration and/or ISI of the sweeps, based on the participant's response. Said another way, in each trial, and in response to the participant's indicated order of the visual sweeps, the stimulus intensity of the visual sweep may be adjusted for the next trial's visual presentation, i.e., based on whether the participant indicated the order of the at least two visual sweeps correctly (or not). The adjustments may generally be made to increase the difficulty of the stimulus when the participant answers correctly, and to decrease the difficulty of the stimulus when the participant answers incorrectly. Moreover, the adjustments may be made such that a specified level of performance, i.e., level of success, is approached and substantially maintained during performance of the exercise. For example, based on the participant's responses, the intensity of the visual sweeps may be adjusted to substantially achieve and maintain a specified success rate, e.g., 85% or 90%, for the participant, although other rates may be used as desired.

In preferred embodiments, the adjustments may be made using a maximum likelihood procedure, such as a QUEST (quick estimation by sequential testing) threshold procedure, or a ZEST (zippy estimation by sequential testing) threshold procedure, described below, such procedures being well-known in the art of stimulus threshold determination. In some embodiments, these adjustments (e.g., using ZEST) may be determined on a per condition basis. In other words, for each condition (used in each task), the visual sweeps may be presented (and adjusted) in accordance with a maximum likelihood procedure (e.g., ZEST) applied to trials under that condition.

Moreover, as described below, the repeating may also include performing threshold assessments in conjunction with, or as part of, the exercise. A description of threshold determination/assessment is provided below.

Threshold Determination/Assessment

As indicated above, stimulus intensity is an adjustable attribute of a presented stimulus whereby the task or a trial in the task may be made more or less difficult. For example, as noted above, in one embodiment, the stimulus intensity may be the duration and/or ISI of the sweeps, although other attributes of the stimulus may be used as desired. The threshold is the value of the stimulus intensity at which the participant achieves a specified level of success, e.g., 0.9, corresponding to a 90% success rate, a 0.85, corresponding to an 85% success rate, and so forth. Note that in some embodiments, the stimulus intensity/threshold may comprise a combination of attribute values of the stimulus, e.g., the presentation time of the sweeps, a combination of duration and ISI, or, as another example, duration, ISI, and contrast (between light and dark bars). In cases where the stimulus intensity is or includes the sweep duration (or presentation time), the adjustment may involve modifying a parameter or attribute of the sweep that corresponds to the duration or presentation time. For example, for the spatial frequency sweeps, the sweep rate or speed may be adjusted, and for the orientation sweeps, the angle range of the sweep may be adjusted. In both cases, this results in an adjustment of duration or presentation time. It should be noted that any other attribute or combination of attributes may be used as desired, the term stimulus intensity being intended to refer to any such adjustable attributes, e.g., color(s) of the sweep, size of the sweep image(s), frequency range of the sweeps, rate of the sweep, a range of cycles/deg for the sweep, etc., among others.

Exercise based assessments (i.e., threshold determination) are designed to assess a participant's threshold with respect to stimuli on a given exercise, and can be used to adjust stimulus presentation to (substantially) achieve and maintain a desired success rate for the participant, e.g., with respect to a particular exercise, task, or condition. As will be described below, such threshold determination may also be used to assess or determine a pre-training threshold that can then be used to calibrate the program to an individual's capabilities on various exercises, as well as serve as a baseline measure for assessing the participant's performance periodically during an exercise. Such assessment may also serve as a baseline measure to which post-training thresholds can be compared. Comparison of pre-training to post-training thresholds may be used to determine the gains made as a function of training with the cognition enhancement exercise or tasks described herein.

As noted above, there are various approaches whereby such thresholds may be assessed or determined, such as, for example, the well known QUEST (Quick Estimation by Sequential Testing) threshold method, which is an adaptive psychometric procedure for use in psychophysical experiments, or a related method, referred to as the ZEST (Zippy Estimation by Sequential Testing) procedure or method, among others, although it should be noted that such methods have not heretofore been utilized in cognition enhancement training exercises using visual stimuli, as described herein.

The ZEST procedure is a maximum-likelihood strategy to estimate a subject's threshold in a psychophysical experiment based on a psychometric function that describes the probability a stimulus is detected as a function of the stimulus intensity. For example, consider a cumulative Gaussian psychometric function, $F(x-T)$, for a 4-alternative-forced-choice (afc) task with a 5% lapsing rate, with proportion correct (ranging from 0-1) plotted against intensity of the stimulus (ranging from 0-5). As used herein, the term intensity (with respect to stimuli) refers to the value of the adaptive dimension variable being presented to the participant at any particular trial in a particular exercise. In other words, the intensity value is that parameter regarding the exercise stimuli that may be adjusted or adapted, e.g., to make a trial more or less difficult. For example, in preferred embodiments of the visual sweep exercise, the intensity value is the sweep duration or presentation time (e.g., in milliseconds). The threshold is defined to be the mean of the Gaussian distribution for a specified success rate—e.g., a value yielding some specified success rate, e.g., 60%, which corresponds to an intensity of 2.

The method may make some assumptions about the psychophysics:
1. The psychometric function has the same shape, except a shift along the stimulus intensity axis to indicate different threshold value.
2. The threshold value does not change from trial to trial.
3. Individual trials are statistically independent.

The primary idea of the ZEST procedure is as follows: given a prior probability density function (P.D.F.) centered around the best threshold guess, x, this P.D.F. is adjusted after each trial by one of two likelihood functions, which are the probability functions that the subject will respond "yes" or "no" to the stimulus at intensity as a function of threshold. Since the psychometric function has a constant shape and is of the form F(x−T), fixing the intensity x and treating threshold T as the independent variable, the "yes" likelihood, p=F(−(T−x)), is thus the mirror image of the psychometric function about the threshold, and the "no" likelihood function is then simply 1−p.

The P.D.F. is updated using Bayes' rule, where the posterior P.D.F. is obtained by multiplying the prior P.D.F. by the likelihood function corresponding to the subject's response to the trial's stimulus intensity. The mean of the updated (or posterior) P.D.F. is then used as the new threshold estimate and the test is repeated with the new estimate until the posterior P.D.F. satisfies a confidence interval criteria (e.g. standard deviation of posterior P.D.F.<predetermined value) or a maximum number of trials is reached.

In one example of the ZEST procedure, a single trial of a 4-afc experiment is performed, with x=2.5 (intensity) as the initial threshold guess. If the subject responds correctly, the next trial is placed at the mean of the corresponding posterior P.D.F., ~x=2.3; if the response is incorrect, the next trial is placed at the mean of the corresponding P.D.F., ~x=2.65.

Thus, in some embodiments, a single staircase (or single stair) ZEST procedure such as that described above may be used to adjust the intensity of the visual sweeps during training. In contrast, in some embodiments, particularly with respect to the periodic assessments during the exercise (as opposed to the "per response" stimulus adjustment) a 2-staircase ZEST procedure may be employed, where two independent tracks with starting values, preferably encompassing the true threshold, each running its own ZEST procedure, are randomly interleaved in the threshold seeking procedure. In addition to their individual termination criterion, the difference between the two stairs may also be required to be within a specified range, e.g., the two stairs may be constrained to be a predetermined distance apart. An exemplary implementation of this approach is described below with respect to the visual sweep threshold assessment.

As used herein, the parameters required for ZEST may include the mean of the prior P.D.F. (threshold estimate), the standard deviation of the prior P.D.F. (spread of threshold distribution), the standard deviation of the cumulative Gaussian distribution (slope of psychometric function), the maximum number of trials to run, and a confidence level and interval. Additionally, in one embodiment, the trial-by-trial data saved for analysis may include: the track used, the stimulus intensity presented, the subject's response, the mean of posterior P.D.F., and the standard deviation of the posterior P.D.F., as well as any other data deemed necessary or useful in determining and/or assessing the participant's threshold.

Thus, in preferred embodiments, a ZEST procedure may be used to adjust the stimulus intensity of the visual sweeps during training (via a single staircase ZEST procedure per condition), and may also be used for assessment purposes at periodic stages of the exercise (e.g., via a dual staircase ZEST procedure, describe below). Thus, in one embodiment, such assessment may occur at specified points during the exercise, e.g., at 0% (i.e., prior to beginning), 25%, 50%, 75%, and 100% (i.e., after completion of the exercise) of the exercise. Thus, for example, in a 40-day exercise schedule, these assessments, which may be referred to as baseline measurements, may be made on days before and after training, and after 10, 20, and 30 days of training, to gauge improvements over the training time. In another embodiment, the training threshold from the daily training is used to generate a recommendation to take an assessment. When the threshold is likely to show an improvement, a recommendation to take an assessment is given. An example of such assessment is now described.

A primary purpose of the visual sweep threshold assessment is to determine the smallest duration of spatial frequency sweeps in a timer order judgment task that a person can respond correctly to above a statistical threshold. The visual sweep assessment may be similar to the visual sweep exercise with respect to visual presentation, where the differences between the assessment and the exercise lie (at least primarily) in the movement or progression through the task and the data that are obtained from this movement for the assessment. The procedure is designed to obtain a threshold, which is a statistical rather than an exact quantity. For the purposes of this exercise, the threshold is defined as the smallest duration of visual sweep (in milliseconds) at which the participant responds correctly a specified percentage, e.g., 69%, of all trials for a serial order judgment task. In a preferred embodiment, being a computer based task, the visual sweep assessment may use the ZEST procedure to progress or move through the task, adjust the duration of the visual sweeps to be presented, and determine the statistical threshold.

As noted above, many aspects of the visual sweep assessment may generally be similar, or possible even identical, to the visual sweep exercise task with respect to visual presentation. However, some aspects of the exercise version of visual sweep may not be necessary in the visual sweep assessment. For example, with regard to the GUI, in some embodiments, one or more of the bonus meter 814 normally displayed on the upper left hand corner, the points indicator 806, and the time remaining indicator 808, may not be necessary, and so may be omitted. Features or assets that may remain the same may include the icons/buttons and the "ding" and "thump" sounds that play after a participant responds correctly or incorrectly. The assessment stimulus presentation may also be identical to the training version.

The following describes one embodiment of a 2-staircase (dual track) approach for determining a psychophysical threshold for a participant, e.g., an aging adult, where the task is directed to spatial frequency sweeps, and where the stimulus intensity comprises the sweep duration or presentation time. Initially, first and second tracks may be initialized with respective durations based on an initial anticipated threshold, where the initial anticipated threshold is an initial estimate or guess of a duration for frequency sweeps corresponding to a specified performance level of the participant, e.g., a stimulus duration at which the participant responds correctly some specified percentage of the time, e.g., 69%. For example, in one embodiment, the first track may be initialized to a first duration that is below the initial anticipated threshold, e.g., preferably just slightly below the initial anticipated threshold, and the second track may be initialized to a second duration that is (e.g., slightly) above the initial anticipated threshold. Thus, the initial durations of the two tracks may straddle the initial anticipated threshold.

Next, as described above in 702 of FIG. 7, first and second spatial frequency sweeps may be provided. For example, a first spatial frequency sweep that increases in frequency over time may be provided, and a second spatial frequency sweep that decreases in frequency over time may be provided. Then, as described in 704 of FIG. 7, at least two frequency sweeps may be visually presented to the participant utilizing the first frequency sweep, the second frequency sweep, or a combination of the first and second frequency sweeps, in accordance with the duration of a specified one of either the first track or the second track. In other words, one of the tracks may be selected or otherwise determined, and the frequency sweeps may be presented with durations of the selected track. As noted above, the frequency sweeps are presented (sequentially) with an ISI (inter-stimulus-interval), i.e., a specified time interval between successive frequency sweeps. In preferred embodiments, the initial anticipated threshold, the first duration, the second duration, and the (to be determined) threshold each includes a respective sweep duration, and a respective ISI. In other words, the term "duration" may be used to refer to the actual sweep duration and the ISI, and so may be a compound parameter or value. In some embodiments, the sweep duration and ISI may be co-varied in the ratio of 1:1. In other words, the sweep duration and inter-stimulus-interval may have the same value, or in some embodiments, may retain the same ratio when varied.

As described above in 706 of FIG. 7, the participant may be required to respond to the at least two frequency sweeps by indicating, utilizing the icons, an order in which the at least two frequency sweeps were presented. In other words, the participant may, in response to seeing the sequence of spatial frequency sweeps, indicate the perceived order of the sweeps.

The duration of the specified track may then be modified, based on the participant's response. For example, the duration of the track may be modified in accordance with a maximum likelihood procedure, such as QUEST or ZEST, as noted above. In one embodiment, for each track, modifying the duration of the specified track based on the participant's response may include increasing the duration if the participant responds incorrectly, and decreasing the duration if the participant responds correctly. As noted above, modifying the duration of a track may include modifying the frequency sweep duration and/or the ISI. Thus, for each assessment trial (in a given track), the duration of the sweep for that trial may be determined by the performance of the previous trial for that track. In other words, the participant's response to the stimulus (spatial frequency sweep) determines that track's next sweep duration via the maximum likelihood method.

Similar to 710 of FIG. 7, the above visually presenting, requiring, and modifying or adjusting, may be repeated one or more times in an iterative manner, but in this case, the repeating is performed to determine respective final durations for the first track and the second track. For example, in one embodiment, trials in the first track and the second track may be performed in an alternating manner, or, alternatively, trials may be performed in the first track and the second track randomly with equal probability. Thus, over numerous trials, the number of trials performed in each track should be equal, or at least substantially equal. In preferred embodiments, the presenting, requiring, and modifying, may be repeated until the durations of the first track and the second track have converged to values within a specified confidence interval, and where the values are within a specified distance from each other, or, until a specified number of trials have been conducted for each track. In other words, the repetition may continue until either some maximum number of trials has been performed, or until convergence conditions for the tracks have been met, both singly, and together. For example, each track may be required converge to a respective duration value (which may include both the sweep duration and the ISI for the track), and the convergent values for the two tracks may be required to be within some distance or interval of each other.

A threshold for the participant may then be determined based on the respective final durations for the first track and the second track, where the threshold is or specifies the duration associated with the specified performance level of the participant. For example, as mentioned above, the determined threshold may specify the duration (sweep duration and/or ISI) at which the participant responds correctly some specified percentage of the trials, e.g., 69%, although it should be noted that any other percentage may be used as desired. In one embodiment, the threshold for the participant may be determined by averaging the respective final durations for the first track and the second track. Note that the assessment approach described above is also preferably applied to Task 2.

Figure 10:
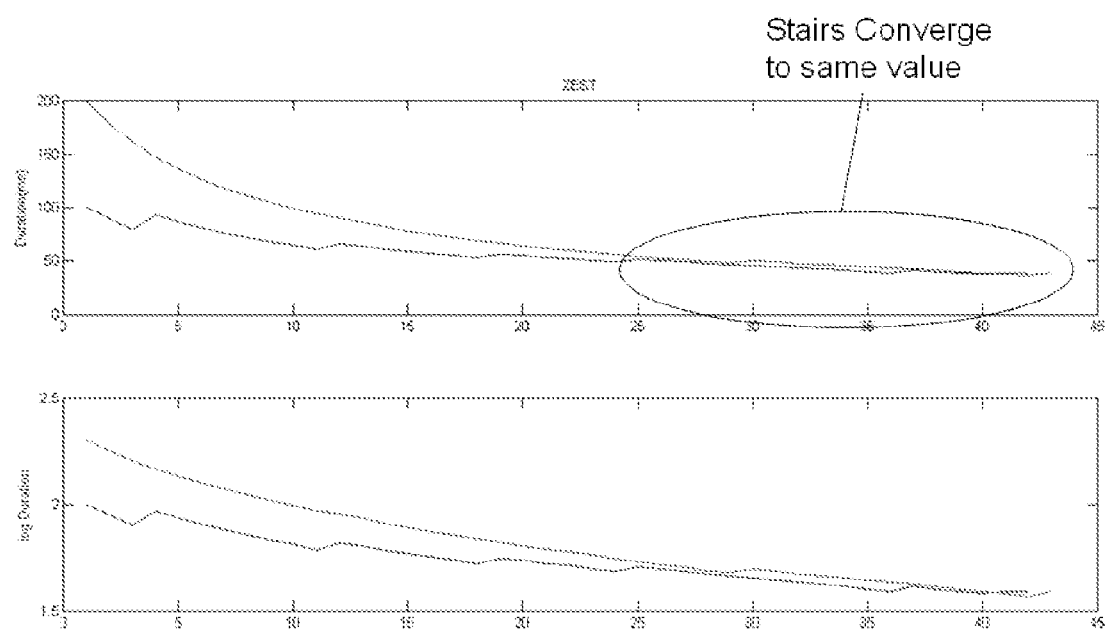
FIG. 10 illustrates convergence to a threshold value over a series of trials in an exemplary two-stair ZEST threshold procedure.

FIG. 10 illustrates an exemplary case where two tracks or "stairs" used in a ZEST threshold procedure are shown converging to a threshold value over a series of trials. Note that in the top graph, sweep duration vs. trials is plotted in a linear manner, whereas the bottom graph provides the same information but is logarithmic on the duration (vertical) axis. As may be seen, after about 25 trials, the two tracks or stairs converge to a value at or near 50 ms, thus, the two tracks, initialized respectively to values above and below an initial estimate of the threshold, converge to an approximation of the participant's actual stimulus threshold for the exercise.

In some embodiments, the presenting, requiring, and modifying may compose performing a trial, and certain information may be saved on a per trial basis. For example, in one embodiment, for each trial, the method may include saving one or more of: which track was used in the trial, the duration used in the trial, the direction and order of sweeps presented to the participant in the trial, the series of icons used in the participant's response (e.g., IN-button, OUT-button, IN-button, and so forth), the correctness or incorrectness of the participant's response, the mean of a posterior probability distribution function for the maximum likelihood procedure, and the standard deviation of the posterior probability distribution function for the maximum likelihood procedure.

Additionally, in some embodiments, various parameters for the maximum likelihood procedure besides the respective (initial) durations of the two tracks may be initialized, such as, for example, the standard deviation of a cumulative Gaussian psychometric function for the maximum likelihood procedure, and/or the standard deviation of a prior threshold distribution for the maximum likelihood procedure.

In one embodiment, the method may include determining the initial anticipated threshold. For example, the initial anticipated threshold may be determined based on one or more of: the age of the participant, calibration trials performed by the participant, and/or calibration trials performed by other participants, e.g., in a "pilot" program, although it should be noted that any other type of information may be used as desired to determine the initial anticipated threshold.

In some embodiments, starting with the first configuration played in the exercise, every eighth configuration may be an assessment. For example, these assessments may appear to be part of the regular exercise, and because the stimulus configurations are almost the same (as those of the exercise), the assessment trials may be used to gauge how much the participant has improved at the task.

In one exemplary embodiment, the characteristics of these configurations may be as follows: The special frequency and orientation may be what may be referred to as the canonical configuration (0 degree orientation; low spatial frequency), although the color may vary. The trial progression may be the exercise algorithm, as described above. The assessments may be compared to the user's initial and subsequent performance. Progress may be measured or characterized by percent improvement, weighted by their time in the exercise. This value may be reflected in a 'recommendation to take an assessment' bar that may appear in the exit screen when the user completes the session. When the participant has met the criteria for an assessment, they may be presented with the option of taking an assessment, e.g., from the exit screen. Once the criteria have been met, the participant may continue to be presented with the option of taking the assessment, until they have opted to take it. Once the user takes the assessment the 'recommendation to take and assessment' bar may reset. Thus, once the participant has met the criteria for being assessed, an assessment option may be presented whereby the participant may invoke an assessment (one or more assessment trials).

As noted above, over the course of the exercise, trials may be performed under each of a plurality of visual sweep conditions. Moreover, such conditions may include baseline conditions used for assessment trials, which, as described above, may be performed at specified points during the exercise to assess the participant's performance, as well as non-baseline conditions used for training trials for cognitive training of the participant. The following exemplary sweep conditions may be suitable for use in the respective tasks of the exercise, although it should be noted that any other conditions may be used as desired.

For the spatial frequency sweep task (Task 1), the baseline condition may include: a black and white (or grayscale) sweep pattern; vertical orientation; and a 1.26-3.18 c/deg range. For the orientation sweep task (Task 2), the baseline condition may include: a black and white (or grayscale) sweep pattern; a medium speed or rate of rotation of the sweep pattern; and 2 c/deg for the sweep pattern. In one embodiment, the threshold level for baseline measurements or assessments is 62.5% and two randomly interleaved adaptive staircases may be used, as described above.

For the spatial frequency sweep task (Task 1), there may be 12 non-baseline conditions, which may include: 3 c/deg ranges (0.5-1.26, 1.26-3.18, 3.18-5); and 4 orientations (90, 0, 45, and 135 deg) for each of these ranges. Similarly, for the orientation sweep (Task 2), there may also be 12 non-baseline conditions, which may include: 4 fixed c/deg values (0.5, 1, 2, 4); and 3 rotation speeds or rates (0.5, 1, 2 deg/sec) for each of the c/deg values.

Thus, for both tasks, there may be 24 non-baseline conditions (12 per task), although other numbers and values of conditions may be used as desired. Note that in some embodiments, for non-baseline trials, i.e., for training trials, the colors used for the sweep patterns may be rotated over 96 training segments (e.g., 24 non-baseline conditions * 4 repeats per condition). In one embodiment, for baseline and non-baseline training taken together, each of 4 colors may be presented an equal number of times overall (e.g., 26 training segments each).

In some embodiments, the patterns will be presented in four colors, and gray may be used for the assessments: Purple: S+, Yellow: S−, Red: L+, Green: M+, and Gray (for assessments). Note that the colors may be chosen so that they maximally stimulate the color channels in visual cortex. Note further that these colors may vary in chromaticity and saturation in different embodiments.

In some embodiments, the method may also include performing a plurality of "eureka" trials during the exercise. These trials may be performed periodically during the exercise, e.g., every 20 trials or so, where each eureka trial may comprise a non-Zest trial that is easier than the current threshold estimate—e.g. 2×threshold). In other words, the presentation time or duration may be twice that currently used in the exercise. In one embodiment, the maximum presentation time for the eureka trials may be 1000 ms, and the minimum may be 10 ms, although other ranges may be used as desired.

In some embodiments, the method may also include performing a plurality of practice trials, i.e., prior to performing the method elements described above. For example, in some embodiments, one or more practice sessions may be performed prior to the beginning of training to familiarize the participant with the nature and mechanisms of each task. For example, in one embodiment, before training begins for each of the spatial frequency and orientation tasks, the participant may perform at least one single sweep session, in which a single visual sweep is presented, and the participant is required to indicate the nature (e.g., direction) of the sweep, and at least one order task practice session, in which a sequence of visual sweeps are presented and the participant is required to indicate the order of the sweeps, as described above. In each practice session, a specified number of trials (e.g., 5) for each of one or more practice conditions may be performed, e.g., where each stimulus pattern is at 2 c/deg. In some embodiments, the participant may be able to invoke such practice sessions at will during the exercise, e.g., to re-familiarize the participant with the task at hand.

Further Exemplary Embodiments

As noted above, in some embodiments, the visual sweep exercise may be presented and performed in the context of a game. In many cases, game play may be essential to the exercise both to help keep participants engaged in the exercise for the full training period and to stimulate key learning neurotransmitters. Thus, games implementing the above visual sweep exercise(s) may serve to train participants across a complete set of non-hierarchical stimulus categories and hierarchical visual emphasis levels ordered into configurations that are integrated with game play so that they can experience the full range of stimuli in an engaging way and realize benefits that generalize to their real-life visual experience. Specifically, game play may be designed to engage the user in the following ways: Focus: learning under conditions of sharp focus promotes the release of acetylcholine; Reward: expectation of reward encourages the release of dopamine; and Novelty, e.g., new and surprising experiences: encountering something new or surprising promotes the release of norepinephrine.

Below are described exemplary games within which embodiments of the above exercise may be implemented, embedded, or encapsulated, although it should be noted that other games may be used as desired. Note that each game may be presented and interacted with via a GUI, whereby progress through the game may be effected and indicated, as will be described below in more detail.

Exercise Games

The following describes exemplary games in which the above Visual Sweep exercise may be embedded or encapsulated. It should be noted, however, that these games described are meant to be exemplary only, and are not intended to limit the games to any particular type or appearance.

Below is described an exemplary embodiment where the exercise is incorporated into a block style game, illustrated in FIGS. 11-14, in which the participant successively clears blocks from a grid by correctly performing trials in a visual sweep task, such as those described above.

Figure 11:
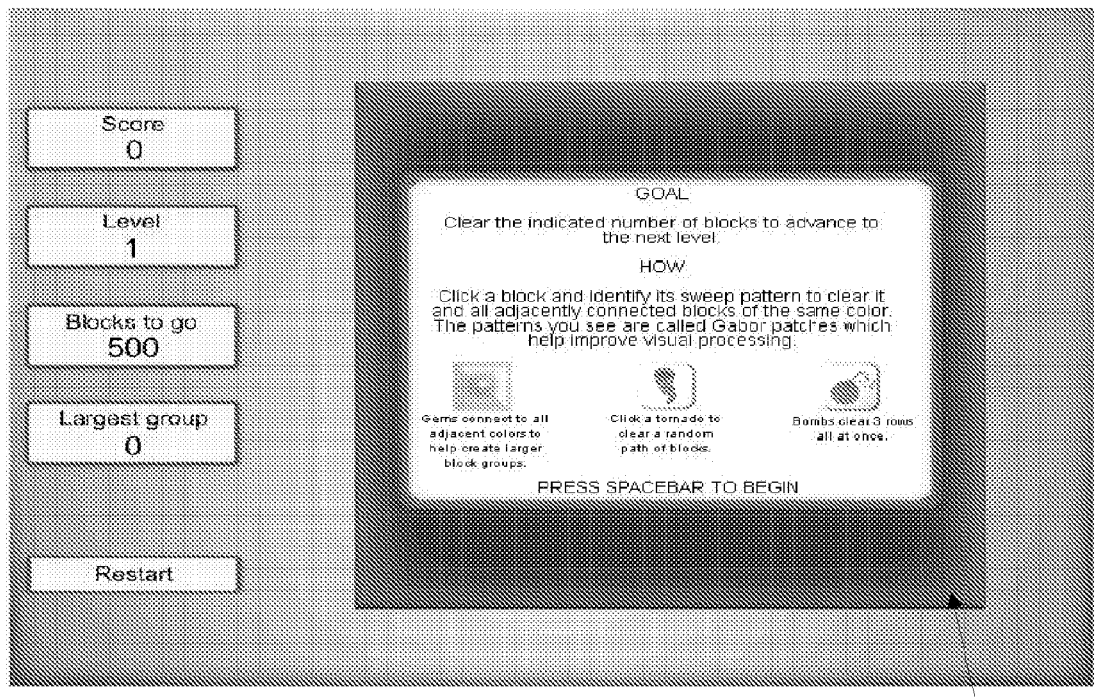
FIG. 11 illustrates an exemplary GUI in which an introductory screen of a block game is displayed, according to one embodiment.

Turning to FIG. 11, an exemplary GUI is shown in which an introductory screen of the block game is displayed. As may be seen, the GUI includes a display area 1102 which, in this introductory screen, displays rules for the game, as well as a number of indicators and controls—specifically, indicators that display the current score, the current level of the game, the number of blocks remaining to be cleared, and the largest group of blocks (of the same color), which in various embodiments may indicate the largest such group currently in the grid, or that has been cleared so far, as well as a button for restarting the game. It should be noted however that these indicators and controls are meant to be exemplary only, and are not intended to limit the GUI to any particular form, function, or appearance.

Figure 12:
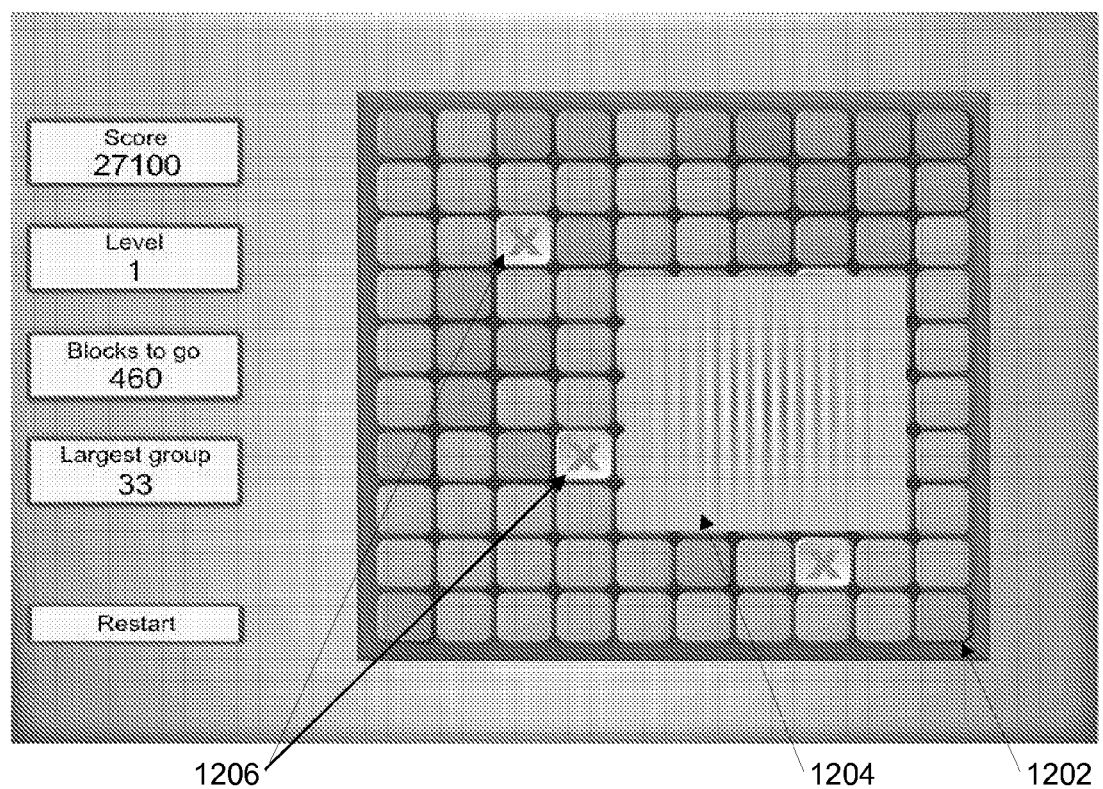
FIG. 12 illustrates an exemplary block grid for the block game, according to one embodiment.

As the displayed instructions indicate, in this exemplary game, the participant may be presented with a grid of colored blocks. FIG. 12 illustrates such a block grid 1202. The participant may select one of the blocks, thereby invoking a trial in a visual sweep task. In one embodiment, as shown in FIG. 12, upon selection of a block, a pop-up window 1204 may be displayed in which one or more stimulus patterns, e.g., visual sweeps, are presented. In other words, the participant may click on a block and visual sweep stimuli may appear in a temporarily expanded box (the pop-up window 1204). As may be seen, in this example, the sweep stimulus utilizes a Gabor pattern, although other patterns may be used as desired. As FIG. 12 also shows, the grid may also include blocks 1206 that were selected previously, but for which the participant did not perform the associated trial correctly. These blocks are shown labeled with an "X".

Figure 13:
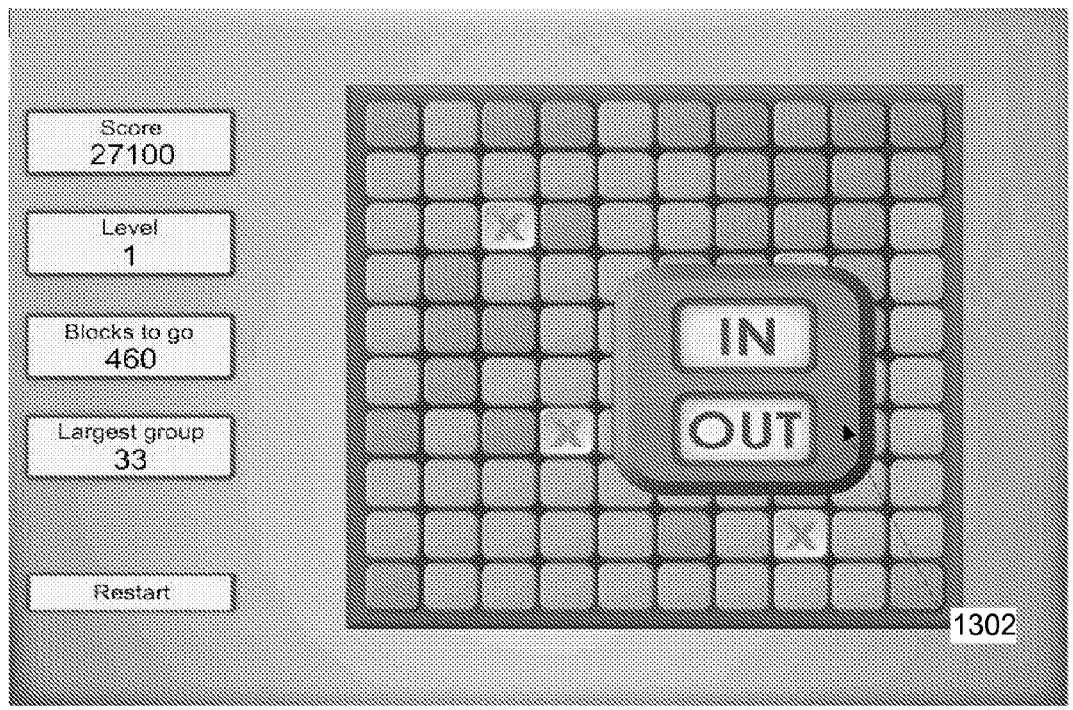
FIG. 13 illustrates an exemplary response box displayed in the GUI for receiving responses from the participant, according to one embodiment.

As FIG. 13 shows, once the stimulus patterns (visual sweeps) have finished a response box 1302 may appear that presents selectable icons or buttons whereby the participant may respond, e.g., by selecting the buttons in a sequence that indicates the order of the presented visual sweeps, as described above. Note that in other embodiments, other means for responding may be used as desired. For example, rather than a response box 1302 that appears dynamically after presentation of the stimuli (visual sweeps), the response buttons may be displayed in the GUI continuously or statically, e.g., below the block grid.

Figure 14:
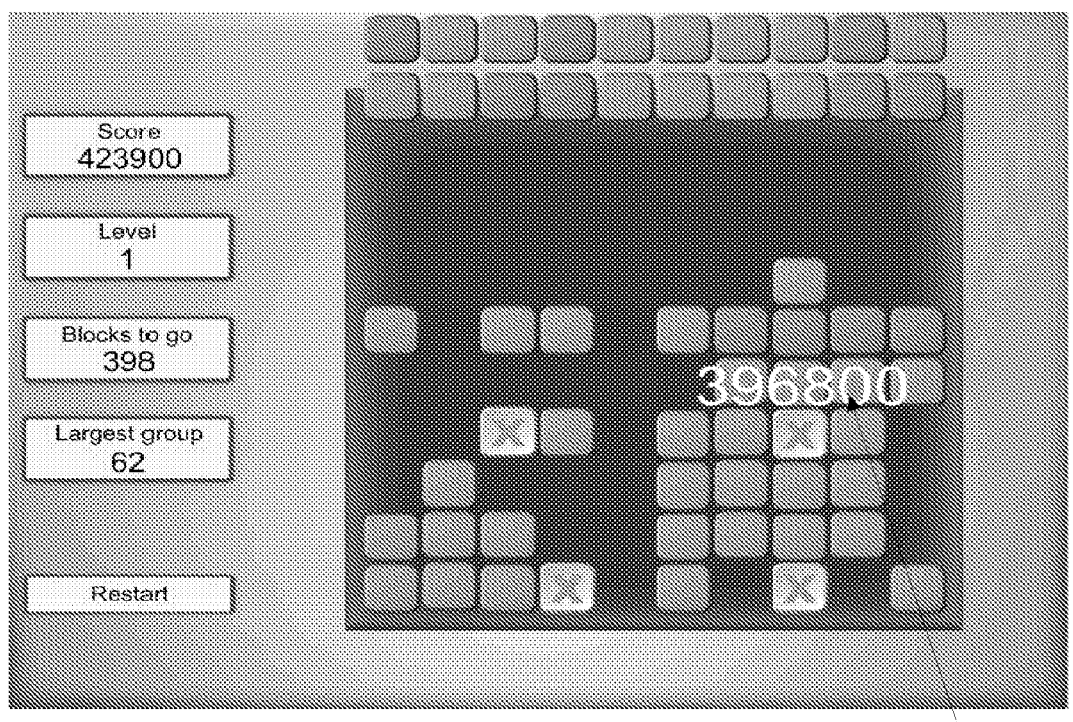
FIG. 14 illustrates an exemplary screenshot of the GUI of FIGS. 12 and 13, but where a number of blocks have been cleared from the grid.

As noted above, if an incorrect response is made, the selected block may be marked by an 'X'. If the participant responds correctly, the selected block and adjacent blocks of the same color may be cleared and additional points received. FIG. 14 illustrates the situation after such a clearing of the blocks and award of points, as reflected by the modified grid and score indicator, respectively.

The following describes an exemplary embodiment where the exercise is incorporated into a tile matching game, illustrated in FIGS. 15-22, in which the participant successively clear tiles from a game board by correctly performing trials in a visual sweep task, such as those described above, or by achieving rows or columns of three or more tiles of the same color. Note, however, that in contrast to the block style game described above, illustrated in FIGS. 11-14, in this game, as tiles are cleared from the board, new tiles are added, i.e., constantly replenishing the tiles. Progression through the game includes performing visual sweep trials under a variety of conditions, referred to as "configurations", that specify such attributes as Gabor pattern orientation, spatial frequency (range), and color of the pattern, although other attributes may be specified as desired. Each configuration may include or specify a plurality of trials using stimuli in accordance with the specified attributes of the configuration.

Figure 15:
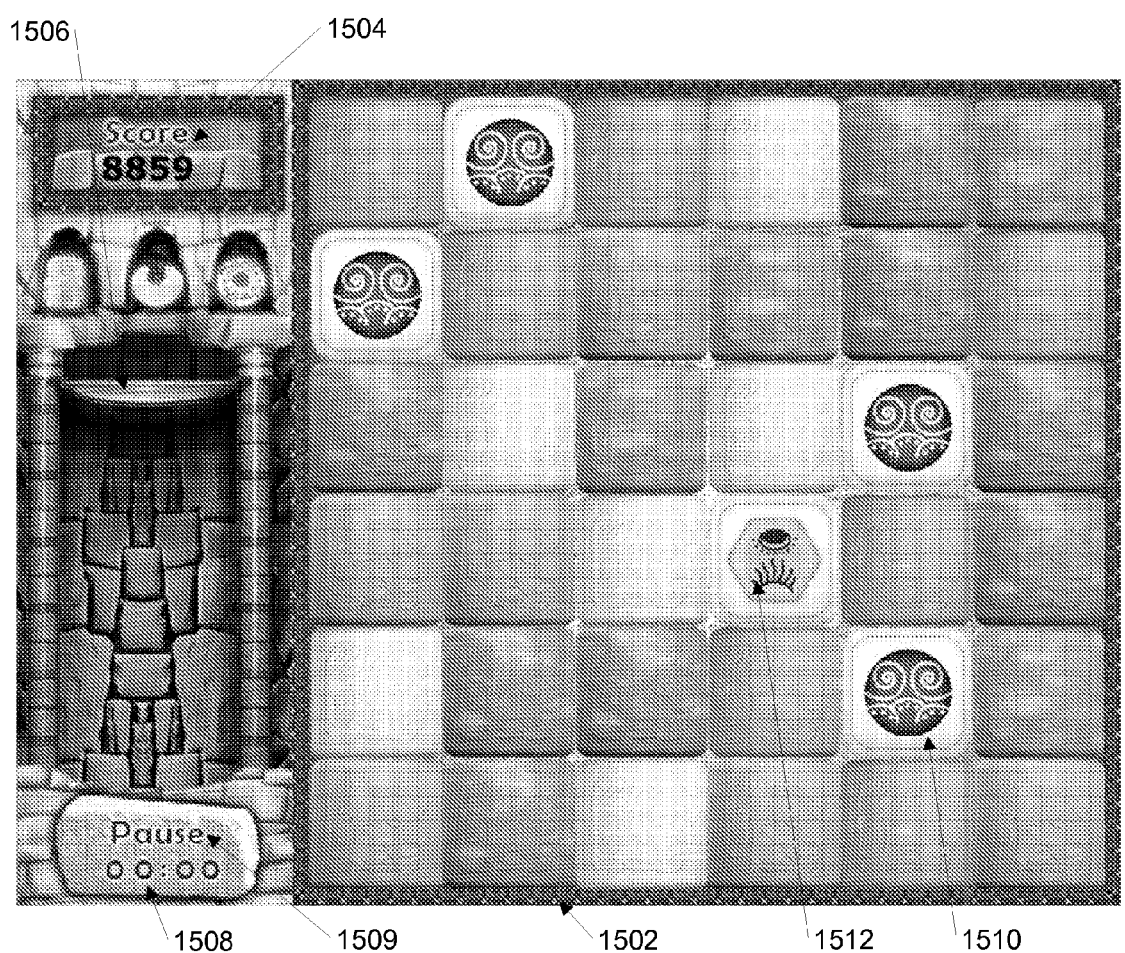
FIG. 15 illustrates an exemplary GUI for a tile matching game, including a tile grid, according to one embodiment.

In one embodiment, the general game process is as follows: a grid of tiles is presented, where each tile has a randomly assigned color selected from a number of available colors, e.g., from four different colors. The game and embedded exercise are played or engaged via a GUI, whereby game and exercise elements are presented or displayed to the participant, and whereby the participant responds, e.g., via buttons, keys, mouse-clicks, etc. FIG. 15 illustrates and exemplary screenshot of the game that illustrates the game board or tile grid 1502, as well as various GUI elements. As may be seen, in this embodiment, the game board 1502 includes tiles of 5 different colors in a 6×6 grid.

In preferred embodiments, the GUI may include various elements indicating the participant's progress in the game. For example, the GUI may include a score indicator (scoreboard) 1504 for displaying accumulated points, i.e., the current score. The score indicator can preferably accommodate 5 digits or more. Moreover, in some embodiments, along with the current score, the scoreboard may show the number of points and tiles cleared in each trial (not shown in FIG. 15).

In some embodiments, the GUI may also include a trial meter 1506 that indicates progress through a current configuration. For example, in one embodiment, the trial meter may comprise a coin scale to which coins may be added, as shown in FIG. 15. Each correct trial may add a coin to the scale, e.g., on the left of the game board, thereby lowering the scale slightly. When the scale reaches bottom (i.e., is full) the configuration is complete and the participant may progress to the next configuration. The number of coins that can be held in the scale determines the exit criteria for the exercises. For example, in one embodiment, the participant may exit a configuration when they have acquired 40 coins, although it should be noted that this value may be different, or may be adaptive based on the participant performance. However, the number of coins needed to exit a configuration is preferably known when the configuration starts. This number may then be used to determine how much the scale should move for each correct trial.

As FIG. 15 also shows, the GUI may also include a timer 1508, where the timer may indicate time remaining in a time-constrained schedule, as well as a pause button 1509, whereby the participant may pause the game, e.g., to assess progress, consider tile selection strategies, and so forth.

Figure 16:
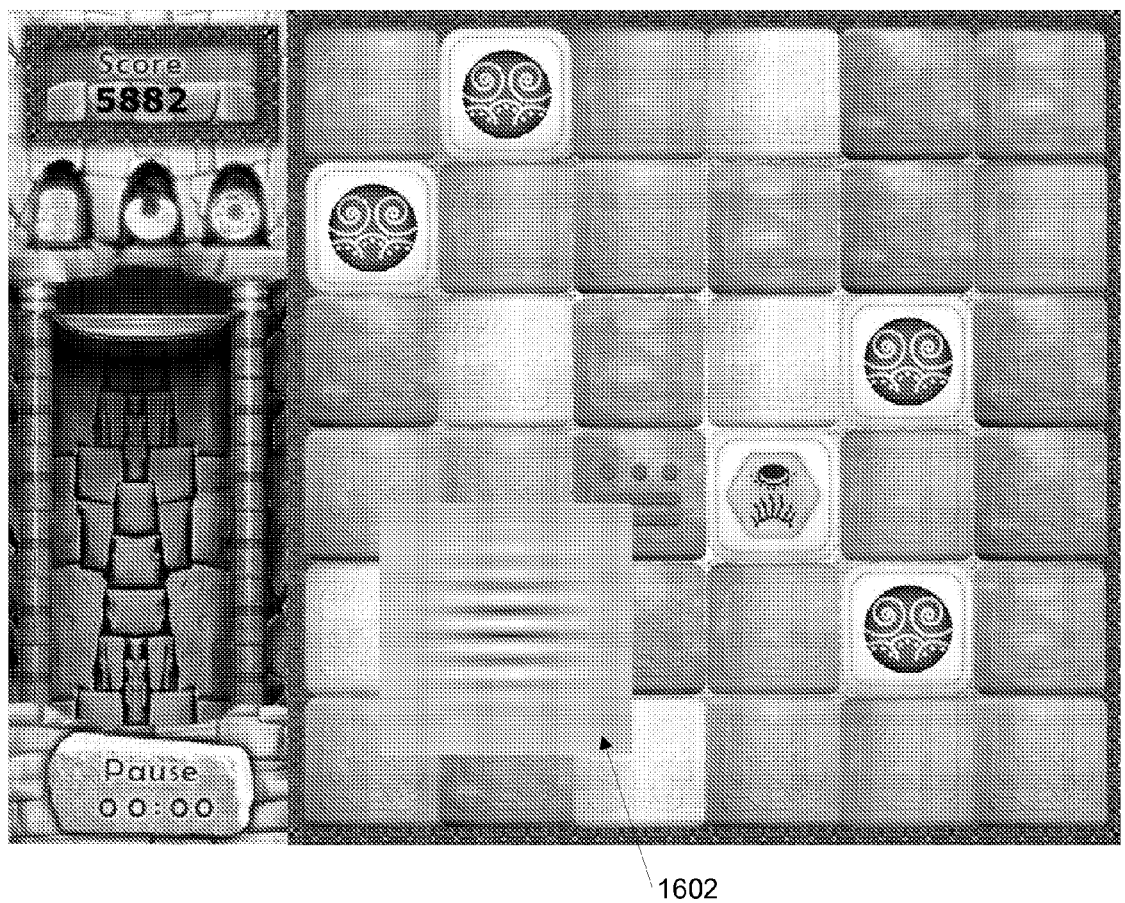
FIG. 16 illustrates an exemplary screenshot of the GUI of FIG. 15, including a visual sweep stimulus, according to one embodiment.
Figure 17:
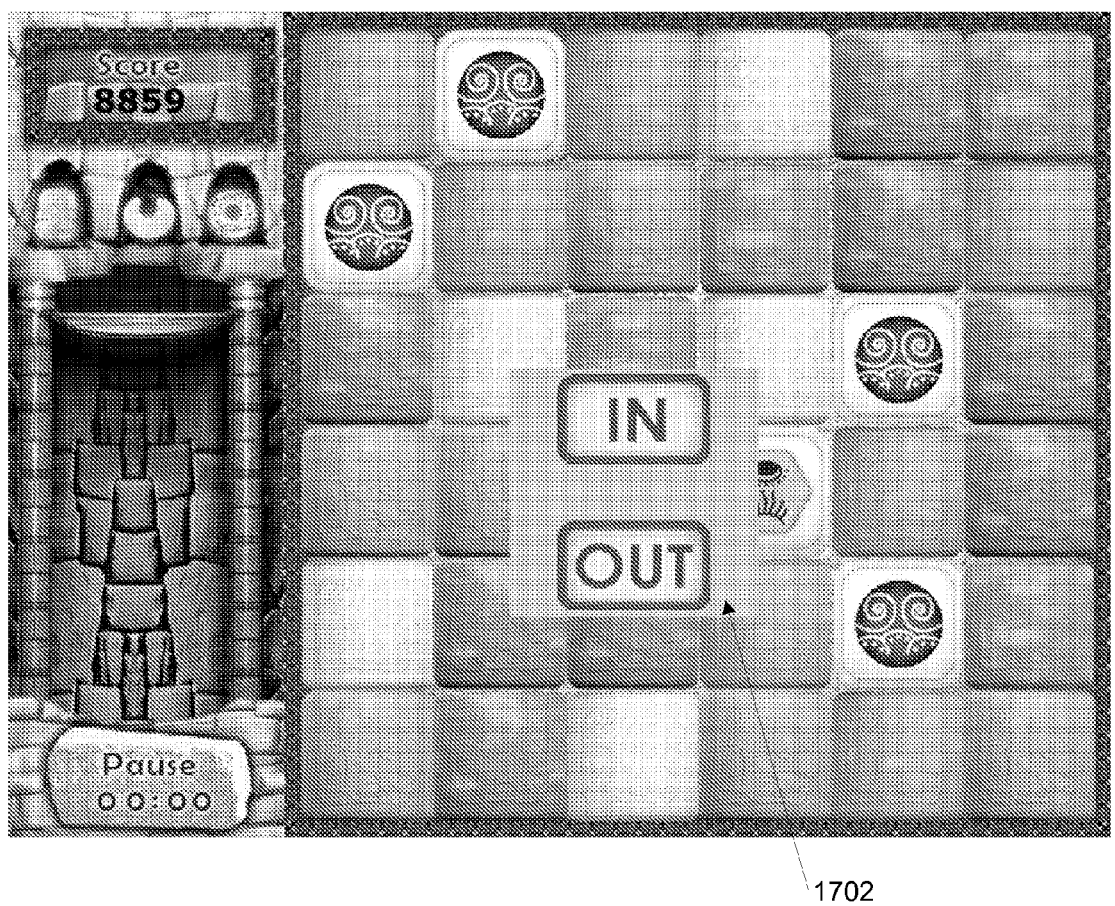
FIG. 17 illustrates an exemplary response box displayed in the GUI of FIG. 15 for receiving responses from the participant, according to one embodiment.

Continuing the general game process, the participant selects a tile (which serves as a "start" button for the trial), and a visual sweeps trial is performed, e.g., a visual frequency sweep trial. FIG. 16 illustrates an exemplary presentation of a Gabor pattern 1602 as part of a visual frequency sweep of a trial, where the trial is performed in response to selection of a tile in the grid. Note that in this embodiment, the stimulus (frequency sweep) is simply overlaid on the game board, although it should be noted that in other embodiments, the trial may be presented in a dialog box, may (temporarily) replace the game board, etc., as desired. FIG. 17 illustrates presentation of a response box 1302 whereby the participant may indicate the direction of the visual sweep, in this case, IN or OUT, as described in detail above.

If the trial is performed successfully, the tile is cleared-possibly with a visually rewarding animation, e.g., illustrating "collapse" of the tile, i.e., the tile disappears, and points are awarded. When the tile is cleared, the tile directly above the original tile "falls" or "slides" down into the vacant position left by the cleared tile, causing the tile above that one to also fall, and so forth, causing a cascade of tile re-positionings in the grid. If these re-positionings result in a sequence of three or more consecutive tiles of the same color (either horizontally or vertically), all the tiles in the sequence may collapse. Thus, during the game, the participant preferably tries to clear tiles to create sets of three or more matching colored tiles. If the trial is performed unsuccessfully, no points may be awarded, and in some embodiment, the tile is inactive or dormant for a specified number of trials, e.g., 3.

As FIG. 15 also shows, in addition to the normal "trial" tiles (the colored tiles), the grid may include, various special tiles, such as treasure tiles 1512 that have an associated treasure reward, and power-up tiles 1510, referred to as "power-ups", that may have any of various effects on the grid. Another type of tile, referred to as a locking tile, may be placed adjacent to power-ups, and must be cleared before the power-up may be activated or accessed. These game elements and more are described in detail below. As the participant plays this game, he or she progresses through visual sweep trials, e.g., visual frequency sweep trials (and/or orientation sweep trials), under a variety of conditions or configurations, as described above. In some embodiments, the game may allow for 48 10-minute sessions (8 hours) of play, where sessions are 10 minutes long, with two configurations played per session. Note that the game play is designed to be integrated with the stimulus configuration in order to challenge participants to move through the full set of visual sweep trials.

Game Elements

The following provides a functional description of elements in the game that the participant can engage, acquire, or otherwise interact with, according to one embodiment. Note that these elements and their characteristics are meant to be exemplary only, and that other elements and/or characteristics may be used as desired.

Tile States

In some embodiments, none of the tiles may have 'down' states. All of the tiles may have rollover states (referring to behavior of the tile when the participant moves the cursor over the tile) with the following exceptions: treasure tiles may never have rollover states and may not be 'clickable'. Power-up tiles may not have rollover states and may not be 'clickable', and additionally, may not slide down when tiles below them are collapsed. Locking tiles for power-ups may not have rollover states and may not be 'clickable.' In addition to this locking tiles may not slide down when tiles below them are collapsed. If a participant gets a stimulus incorrect the tile they click may become dormant and may not have a rollover state until the dormant state is cleared. When the tile is in this state it may not respond to participant clicks.

Correct Trial

When the participant correctly performs a trial, the tile may collapse, a coin may pop out of the tile and a sound may be issued or played (indicating success). The coin may be added to a scale that contains coins, e.g., displayed on the left-hand side of the screen. When the scale reaches the bottom of the screen the configuration may be considered completed. The stack has room to accommodate some specified number of correct trials, e.g., 40 (e.g., accommodating 40 coins). Each correct response may add points to the score. If the trial results in further collapse, a graphical effect, e.g., a particle system animation, may accompany each successive collapse and additional points may be awarded.

Incorrect Trial

If the participant incorrectly performs the trial, a sound may be issued (indicating failure) and the tile may change to a muted color, e.g., may change to a dormant state. The participant may not be able to click on the tile until some specified number of trials, e.g., three, have been completed (regardless of whether the participant performs the trials correctly or not). The tile may contain a counter that may indicate to the participant how close they are to freeing the tile from the dormant state. The update to the tile counter may happen at the same time a participant initiate a trial. If the trial frees the tile from the dormant state, the tile state may be reset and a graphical effect, e.g., a particle system animation, may be initiated. This may only happen after the participant responds to the current stimulus set and all collapsing tiles are resolved. Dormant tiles can be collapsed if they are part of a group of three or more matching colors. In other words, by aligning three or more tiles of the same color (either horizontally or vertically), the tiles may collapse, and so the participant may clear those tiles without performing the trials normally required to clear them. Note that no points may be awarded for an incorrect trial and no coins may be released.

Regular Tiles

Tile layouts may be able to support irregularly shaped game boards (e.g. layouts other then rectangular). A correct trial may result in a tile being removed from the game board. As indicated above, any of the tiles that are above the collapsed tile may move down, and new tiles may be added to fill in the gaps above the collapse. In preferred embodiments, the cascading motion of the tiles as they collapse may be smooth and may occur over 2 or 3 frames. As also noted above, if three or more tiles have the same color and are adjacent to each other (vertically or horizontally) they may collapse. When this happens a graphical effect, e.g., a small particle system animation, may be presented to draw the participant's attention to the collapse and a unique sound may be issued. While tiles are collapsing and moving into their new positions the participant may not be allowed to engage in a trial.

Tile Collapsing Rules

When tiles are collapsing any rollover state may be reset, and rollover states may not be active while the collapsing is occurring. Similarly, the participant may not be allowed to click on any of the tiles while they are collapsing. Once the last tile has stopped moving, all of the tiles may be reviewed for additional collapses. For example, the tiles may be checked for three or more in a row of the same color. If additional collapses are detected, the blocks may be collapsed and additional blocks may be added.

Filling in Eliminated Tiles

Figure 18:
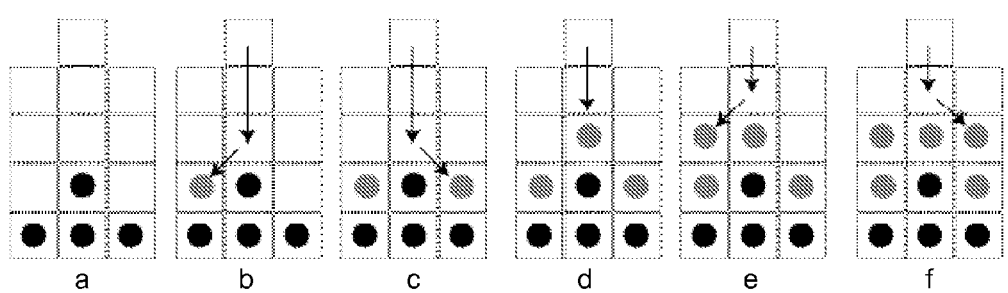
FIG. 18 illustrates various ways in which tiles may adjust to a new space to fill, according to one embodiment.
Figure 19:
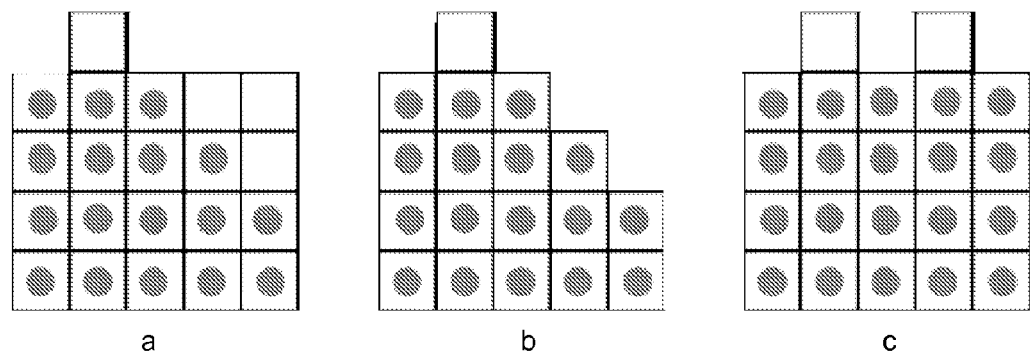
FIG. 19 illustrates inaccessible slots in a grid layout and possible solutions, according to one embodiment.
Figure 20:
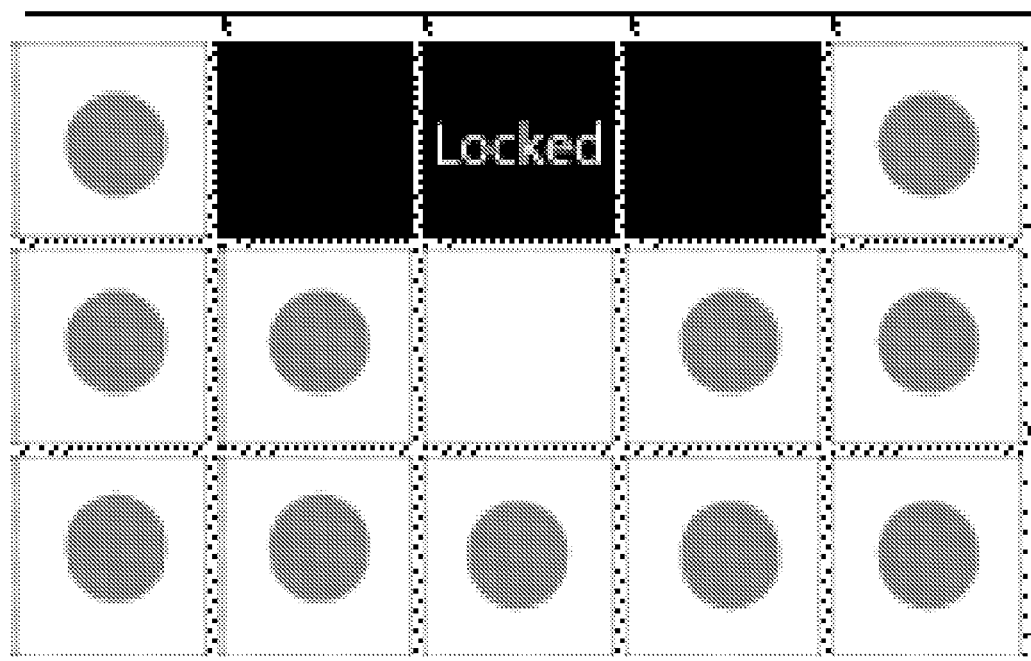
FIG. 20 illustrates an invalid configuration of locked tiles, according to one embodiment.

When a tile falls the following rules may be used to determine the next position to move to. Tiles may continue to move down until they hit an obstruction (e.g., a locked tile or a game board border). FIG. 18(a-f) illustrates various ways in which tiles may adjust to a new space to fill. FIG. 18a shows a tile configuration where the opening or entry point for new tiles is at the top of the middle column of a three column grid (or grid portion). As FIG. 18b shows, if there is an opening to the left of the tile it may move diagonally to fill the space. If there is an opening to the right of the tile it may move right to fill the spot, as shown in FIG. 18c. If there are no openings the tile may stay at rest in its landing position, as illustrated in FIG. 18d. FIGS. 18e-f illustrate these same principles applied a second time, e.g., after the moves of FIGS. 18b-d.

Limitations: Note that in some cases, the rules and mechanisms presented above may limit the amount of area that can be filled. For example, in cases where there is only one opening through which new tiles are added to the grid, only the area shaped in a cone below the opening can be filled. FIG. 19a illustrates this issue, where, as shown, the area (three slots) in the upper right of the grid cannot be filled by cascading tiles entering through the opening or entry point at the top of the second column (counting from the left). There are (at least) two solutions to this problem. First one can simply modify the layout or shape of the grid to accommodate the limitation, e.g., by removing tile slots or positions that are inaccessible to the opening or entry point, as shown in FIG. 19b; or, one may simply add an additional one or more openings or entry points, as illustrated in FIG. 19c, where there are two openings or entry points, such that every slot in the grid is accessible or available for positioning of tiles.

Note that in some embodiments, there may never be more then three locked tiles in a row, e.g., possibly as a result of the above rules. This may have implications for how power-ups are constructed, making constructions like that shown in FIG. 20 impossible to fully support. As may be seen, in this configuration, no further movement of tiles is possible, since the only open space is effectively blocked both from above and on each side.

Treasure Tiles

As noted above, some tiles may contain treasures locked inside of them (see, e.g., tile 1512 of FIG. 15). The participant may not be able to directly click on these items, but may be able to unlock them by collapsing them in groups of three, horizontally or vertically aligned. When the treasure is released it may animate to a side bar of the GUI, and a tally may be incremented to indicate that the participant unlocked the treasure. Moreover, additional points may be added to the score in addition to the point for the correct trial and the collapsed tiles. If more then one treasure is unlocked at the same time the participant may receive credit for all unlocked items. In some embodiments, the introduction of treasure items may increase over time, but may not be available in initial configurations, e.g., in the first four configurations. In one embodiment, a maximum of three types of treasure may be available in any configuration. As one example, a treasure tile may appear with a specified frequency, e.g., 5%. Thus, in this example, when new tiles are added to the board a treasure tile may appear 5 times out of 100.

In some embodiments, the frequency of each of the treasure tile types may be distributed in the following manner, although other frequencies may be used as desired. In scenarios or configurations where there is one treasure, 15% of the tiles may be treasure tiles of a first type. In scenarios or configurations where there are two treasures, 10% of the tiles may be of the first type of treasure tile, and 5% may be of a second type of treasure tile. In scenarios or configurations where there are three treasures, 10% of the tiles may be of the first type of treasure tile, 4% may be of the second type of treasure tile, and 1% of the tiles may be of a third type of treasure tile. Note that each treasure tile type may have a respective type of treasure. Each treasure type may appear at least once in each completed configuration.

Achievements

In some embodiments, during the game, various achievements may be met by the participant with respect to different aspects of the game. These achievements may help motivate the participant to continue through the exercise, and may provide further mechanisms for reward. For example, each time an achievement is met, a reward, such as a congratulatory message or display may be presented to the participant. An exemplary list of such achievements is provided below, although other achievements may be used as desired.

Tracking progress against an achievement can be difficult when a configuration spans multiple sessions. In some cases it may be desirable to save the progress towards the achievement from one session to the next, whereas in other cases this may not be desirable. For example if the participant is trying to complete a configuration in under 3 minutes, the participant may want to remember how much time was spend in the configuration upon exiting. On the other had, if the participant is trying to successfully perform eight trials in a row, the participant may not want the information persisted from one session to the next. Each achievement type may have an indication as to whether the related information for that achievement should persist or not. Note that the game may include various achievements or metrics of success that allow the participant to achieve success with respect to a number of different aspects, including, for example, number of successful trials in a row, overall success rate, success with respect to trials of specified (and increasing) difficulty, and so forth. Exemplary achievements are provided below, although other metrics may be used as desired.

Correct Trails in a Row (information may not persist from session to session): one level of achievement may be met if the participant performs 7 trials in a row correctly. A second level of achievement may be met if the participant performs 10 correct trials in a row Points (information may persist from session to session): a first level of achievement may be met if the participant gets more then 10,000 points in a configuration. A second level of achievement may be met if the participant gets more then 15,000 points in a configuration. A third level of achievement may be met if the participant gets more then 20,000 points in a configuration.

Game Level Comparison (information may persist): all of these achievements may be based on the best score in the previous game level. Game levels may be advanced per some specified number of configuration, e.g., every 32 configurations. A first level of achievement may be met if the participant completes a configuration in less time then their best time in the previous game level. A second level of achievement may be met if the participant finishes the configuration in less trials then they did in the previous game level. A third level of achievement may be met if the participant gets a higher score then their best score in the previous game level Number of Tiles (information may not persist): This achievement may be met if the participant correctly performs the number of trials required to complete a configuration in less than some specified total of trials, e.g., if 40 correct trials are required to complete a configuration, and the participant correctly performs the 40 trials in a total of 48 trials, say, instead of an allowed 60 trials.

Treasures (information may persist): This achievement may be met if the participant collects more than some specified number of treasures in a configuration, e.g., 14 treasures in a configuration.

Tiles (information may not persist): A first level of achievement may be met if the participant collapses more than some specified first number of tiles in a single trial, e.g., more than 8 tiles in a single trial. A second level of achievement may be met if the participant collapses more than some specified second number of tiles in a single trial, e.g., more than 10 tiles in a single trial. A third level of achievement may be met if the participant collapses more than some specified third number of tiles in a single trial, e.g., more than 12 tiles in a single trial.

Time (information may persist): This achievement may be met if a participant completes a configuration in under some specified time, e.g., under 3 minutes.

Introduction of New Game Elements

In some embodiments, the participant may be provided an introduction to the game elements in one (or both) of two different ways. In a first approach, the participant may be introduced to the game elements in an instruction screen that may appear the first time the game is entered. This screen may introduce the basic game concepts and facilitate the participant starting the game. In some embodiments, the instruction screen may also include a general overview of game aspects such as multiple collapses, treasure tiles, and power-ups, among others. The participant may be able to access the instructions screen any time, e.g., from a menu in the GUI.

In some embodiments, in addition to the instructions page the participant may be presented with in-game prompts that may introduce new gaming concepts as they are brought into the game. What follows are a list of areas that may require additional explanation. The information may be presented in a text format, graphically, and/or via animated sequences. Note that some of these items may require instruction only when they are first introduced to the participant. Thus, if the participant has completed the entire game and cycles back to the beginning it may not be necessary to re-introduce these elements. An exemplary list of main points for intervention (in-game explanation) may include, but is not limited to:

Introduction of the game navigation: This explanation may include how to access the side bar menu system and what type of information to look for in the side bar. This should only appear the first time a participant enters an exercise First time issuing a trial: e.g., click button or tile to start a trial.

First time getting a trial incorrect: This explanation may include information about why the tile is inactive and when it may become active again.

The first time an incorrect trial tile becomes active again.

First time a treasure piece is introduced to the game board.

First time a power-up is acquired.

First time a power-up is activated.

First time the participant is presented with a configuration summary screen.

Points

Points in the game may be awarded using any of a number of schemes. The following presents one such scheme, although other schemes may be used as desired. Note that the scheme below is presented in terms of an elementary point increment, P, which may initially be set to a value of 2, but which may subsequently vary by configuration or other rules.

Action points may be awarded according to the following scheme:

TABLE 1

| Action | Points Awarded |
| --- | --- |
| Clear single tile | P |
| Clear a row or column of 3 tiles | Number of tiles cleared * P |
| Clear a row or column of more than 3 tiles | Number of tiles cleared * P |
| Clear a connected row and column of tiles | 2 * (number of tiles cleared * P) |
| Clear multiple unconnected rows or columns of tiles | Number of tiles cleared * P |
| Unlock a power-up | 2 * P |
| Use a power-up | Number of tiles cleared * P |
| Clear treasure tile | P (more points stored for bonus) |

As indicated in the last entry of Table 1, when treasure tiles are cleared, additional points, i.e., bonus points, may also be awarded, as described below in Table 2.

Bonus points may be awarded for cleared treasure tiles, and may be added to the participant's score at configuration transitions, i.e., upon exiting a configuration. Bonus points may be awarded in increments of P points. Table 2 presents an exemplary scheme used to award bonus points based on the type of treasure acquired, i.e., based on the type of treasure tile cleared.

TABLE 2

| Treasure | Bonus Points Awarded |
| --- | --- |
| T1 | 2 * P |
| T2 | 4 * P |
| T3 | 6 * P |
| T4 | 8 * P |
| T5 | 10 * P |
| T6 | 12 * P |
| T7 | 14 * P |
| T8 | 16 * P |

Power-Ups

Power-ups (see, e.g., element(s) 1510 of FIG. 15) may offer participants an alternative method of clearing tiles from the game board. For example, each game level may have 3 or 4 power-ups that may be introduced into the game play on a regular schedule. The power-up may include the power-up tile and supporting locked tiles that may need to be solved before the participant can activate and use the power-up.

Figure 21:
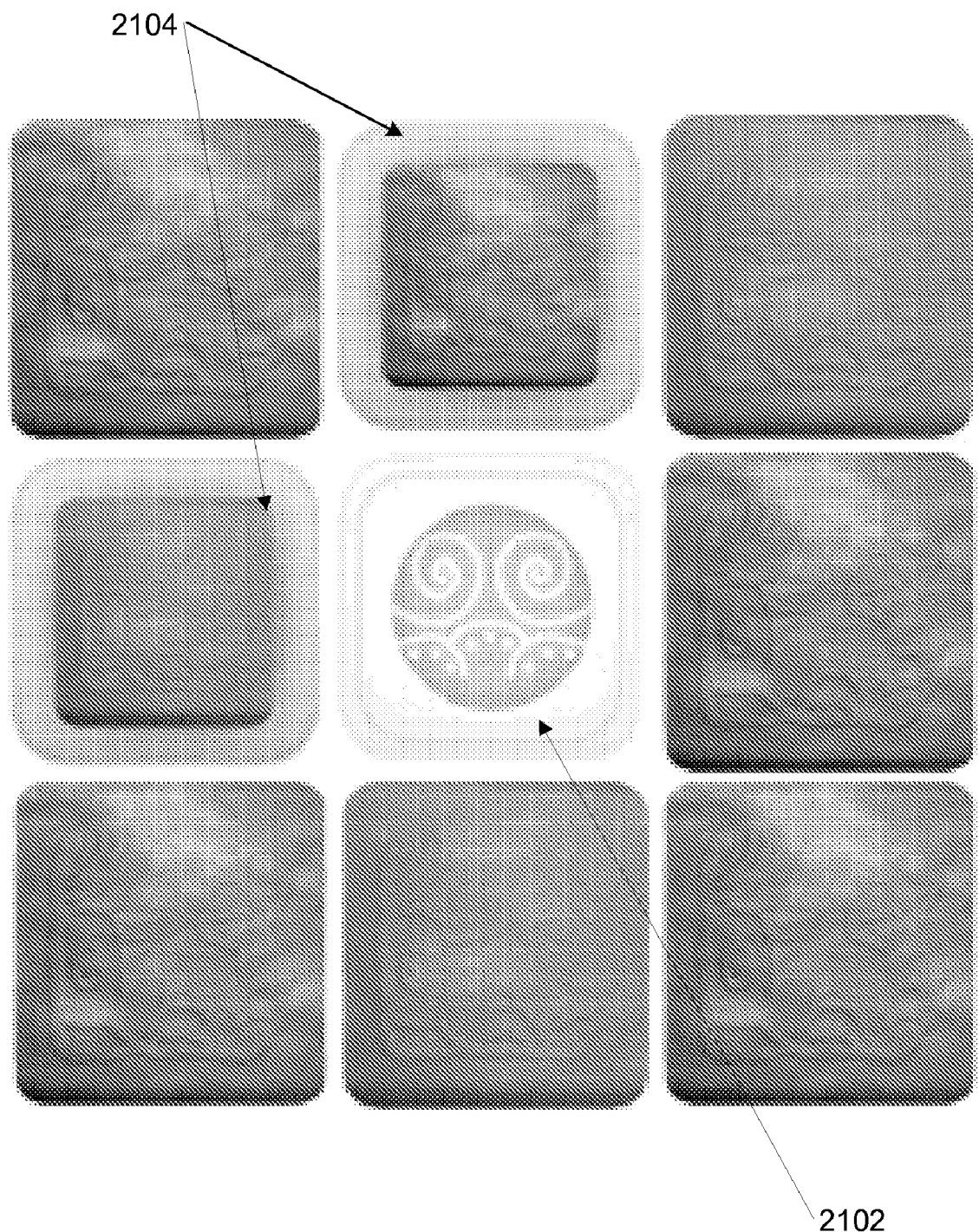
FIG. 21 illustrates a power-up tile with adjacent locked tiles, according to one embodiment.

Each power-up tile may be surrounded by 1-3 locking tiles that must be cleared before the power-up can be used. FIG. 21 illustrates this concept. As shown, the center tile 2104 is the power-up tile and the tiles 2104 above and to the left of it are the locking tiles. Note that the locking tiles preferably do not move from their respective locations unless they are collapsed. Thus, considering the arrangement of FIG. 21, if the bottom row of tiles were to be cleared, the locking tiles would not fall to a lower row, but rather, would stay where they are located. In preferred embodiments, the only way to remove a locking tile from the board is to collapse it by matching three (or more) colors in a row. Thus, in the example of FIG. 21, if the tile in the upper right corner were blue, the row would collapse and the locking tile would be cleared. Once all locking tiles adjacent to a power-up are cleared the power-up may become active. Locking tiles may behave according to the following rules:

Locking tiles may have an appearance that identifies them as part of the power-up, such as shown in FIG. 21. Initially the power-up tile and the locking tiles may not be clickable, and so a participant cannot solve the tile by clicking on it to invoke and perform a trial correctly. As noted above, the participant may only eliminate the locking tiles by re-arranging other tiles in such a way that the locking tile is part of a three (or more) in a row combination. When this happens the locking tile collapses, along with the others in the row (or column). When all locking tiles that are adjacent to a power-up have been cleared, an animation, e.g., a particle effect, may be presented, and the power-up may transition from its dormant state to an active state that a participant can then click on. Power-up and locking tiles may not move like normal tiles. For example, in preferred embodiments, they may be placed on the game board at startup and may not change position until they are cleared or solved. If one or more tiles below the power-up or locking tiles are solved, tiles from the side may flow in to fill the new spaces in the game board.

Initially, the power-up tile may appear in its dormant or muted state, and may not have a rollover state or respond to a participant click. Once a power-up tile is unlocked, e.g., by clearing the adjacent locking tiles, the appearance of the power-up may change, an animation, e.g., a particle effect, may be presented to signify that the power-up is activated, and the power-up may then respond to rollovers and mouse-clicks. If a participant clicks on a power up when it is active, a normal trial may be invoked. If they perform the trial correctly, the tile may exercise or unleash its power, examples of which are provided below. If the participant performs the trial incorrectly, some number of the surrounding tiles (e.g., 1-3, depending on the game level) may become locking tiles, and the power-up may returns to its dormant or muted state.

The type of power-up's available and the number of locking tiles associated with them may be determined by a specified schedule or scheme. The power-ups may accumulate over time in each game level, so that once a power-up is introduced into game play there is a possibility that it may be available on every successive configuration until the game level changes. Once the game level changes an entirely new set of power-ups may be used. Table 3 presents the types of power-ups, the configurations in which they appear, and the number of locking tiles associated with them, although it should be noted that the schedule is meant to be exemplary only, and that other schedules and schemes may be used as desired.

TABLE 3

| Configuration | Power-Up | No. On Screen | No Locking Tiles |
| --- | --- | --- | --- |
| 1-8 | — | — | — |
| 9-16 | Earthquake | 1 | 1 |
| 17-24 | Fire Fly | 2 | 1 |
| 25-32 | Corn | 3 | 1 |
| 33-40 | Typhoon | 1 | 2 |
| 41-48 | Lighting | 2 | 2 |
| 49-56 | Quicksand | 3 | 2 |
| 57-64 | Might Wave | 3 | 2 |
| 65-72 | Resurrection | 1 | 3 |
| 73-80 | Arrow | 2 | 3 |
| 81-88 | Dust Storm | 3 | 3 |
| 89-96 | Destructive Force | 3 | 3 |

The effects of these various power-ups are described below, although it should be noted that the power-ups described herein are meant to be exemplary only, and that other power-ups with other effects may be used as desired.

Because power-ups have specific functionality, and because they never move, they may follow specific rules, as follows. Power-ups may never be added in the middle of a configuration. All power-ups may be placed on the board when the configuration starts. Power-ups may be placed towards the center of the game board. Moreover, they may be placed such that they always have at least 2 rows of tiles above them and at least 1-2 to columns of tiles on either side. There may never be more then two horizontally consecutive locking tiles. Once a power-up is used it may be removed from the game board. Power-ups may be placed at least two rows and two columns away from each other. As noted above, no power-ups may be available in the first eight configurations.

Example Power-Ups

The following provides a description of the visual effect of each of the above power-ups and the effect each power-up has on the game board. Each of this effect may operate over a relatively short period of time (e.g., 3-5 seconds), and once the effect is completed the game board may check for collapses and add tiles as needed. In some cases these descriptions refer to a specific animation or special effect, although other animations or effects may be used as desired.

Earthquake: When the Earthquake power-up is activated all the tiles on the game board may start shaking. At first the shaking may only involved displacements of 1 or 2 pixels, but may increase over time to 10-15 pixels. This may be followed by an animation, e.g., a particle effect, at which time every tile on the board may be swapped with another tile on the game board. The pattern for swapping may be random. Note that this effect may not change the position of locked tiles or power-ups.

Fire Fly: When this power-up is activated a glowing ball may be released from the tile and begin moving in a random direction. The motion may be defined by a specified function or model, e.g., a sine particle wave model, and a tail may extend from the ball. As the ball moves the tile below the object may glow yellow for a short time then slowly fade to a new color. Once the tile turns completely to the new color a small burst may be displayed or released. The color the tiles change to may be selected at random, but all tiles touched preferably change to the same color. When the glowing ball leaves the game board it may explode into a small particle burst.

Corn: This power-up may release 2-3 balls into the neighboring tiles. The balls may bounce up into the air ("out of the board") and strike the neighboring tiles in the center. When the balls land on the neighboring tile, 2 or 3 additional balls may be spawned and may behave in a similar manner. None of the spawned balls may travel back in the direction from which they came. Each time a ball hits a tile, the tile may change to a color that is randomly selected when the power-up is activated.

Typhoon: This power-up may release an effect, e.g., a spinning particle effect, that may cover a diameter of 5 tiles. As the effect picks up speed each of the tiles in the area may be picked up and may start spinning around the center of the power-up. When the effect finishes the tiles may be placed back on the grid or board in a different order. Note that this effect preferably does not alter the position of power-ups or locking tiles.

Lightning: A lightning power-up may release a bolt of lighting and collapse all tiles that are in the same row as the power-up. Additionally, all of the tiles in the row directly above or below the power-up may be destroyed. If the effect collapses treasure tiles then the normal behavior defined for the collapse of these tiles may be followed. The effect may also collapse tiles that are dormant or muted due to incorrect responses. Note that this effect preferably does not affect other power-ups or the locked tiles surrounding a power-up.

Quick Sand: This power-up may release a swirling particle system centered on the power-up. All the tiles in a 2-tile radius may begin to shrink and be pulled into the center of the vortex, although power-up and locked tiles may not be affected. Once all the tiles have been pulled into the center a shockwave particle system may be released.

Might Wave: When the might way is activated the tiles in the bottom row may pull back 10-15 pixels, then release forward. This effect may then cascade to the next row and work its way across the entire game board. As the rows move forward all of the tiles that are of a specified color may flip and become a different color. Thus, for example, all red tiles may flip over and become a random color. Locked tiles may not be affected by this power-up.

Resurrection: This power-up may give the participant the ability to randomly resurrect one of the previous power-ups. When this power up is activated the tile may start cycling through all of the previous power-up types. The sixth (or some other specified) tile in the sequence may freeze on the screen and display the 'hidden' power-up. When the participant activates the power-up it may have the behavior of the power-up it represents.

Arrow: When this power-up is activated, 8-15 arrows may shoot straight up into the air (e.g., "out of the board"). Each of the arrows may land in the middle of one of the surrounding tiles and change the color of the tile to a pre-determined color.

When the color changes a small particle effect may be released. The arrows may never strike power-ups or locked tiles.

Dust Storm: This power-up may create a dust storm that may travel up, down, left or right of the power-up. The direction of travel may be based on the direction that allows the storm to travel the greatest distance. When it is activated the tiles around the power-up may release a particle system that travels in the direction of the storm. Over time, the downwind tiles may start releasing similar particles effects until the storm reaches the end of the game board. As the tile releases its particle system the tile may slowly start to change its color to a pre-determined color that may be shared with all tiles in the storm. Power-up and locked tiles may not be affected by this effect.

Destructive Force: When activated, this power-up may release a shockwave particle system and collapse all tiles within a 3-tile radius of the power-up. Power-up and locked tiles may not be affected by this effect.

Game Flow, Levels, and Asset Revelation Schedule

The following describes an exemplary game flow, specifying configurations and levels in the game, as well as assets associated with each configuration. As noted above, in this embodiment, the exercise has 3 game levels, each of which has 32 configurations. Each of the game levels represents a different region of the game. The first region is Mayan, the second Oceania and the third centers around Pueblo Indians, although these are meant to be exemplary only. Table 4 represents the progression of backgrounds, game board layouts, power-ups and treasures as they relate to configurations in the Mayan world, i.e., level 1. Table 5 provides this information for subsequent levels.

TABLE 4

| Map 1 | Config. | Background | Layout | Power-ups | Treasures |
|---|---|---|---|---|---|
| First location | 1 | 1 | Easy | None | None |
|  | 2 |  |  | 2 |  |
|  | 3 |  |  | 1 |  |
|  | 4 |  |  | 2 |  |
| Second location | 5 | 2 | Med. | 1 | None | 1 |
|  | 6 |  |  | 2 |  |
|  | 7 |  |  | 1 |  |
|  | 8 |  |  | 2 |  |
| Third location | 9 | 3 | Hard | 1 | 1 | 1, 2 |
|  | 10 |  |  | 2 |  |
|  | 11 |  |  | 3 |  |
|  | 12 |  |  | 4 |  |
| Fourth location | 13 | 4 |  | 5 | 1 | 1, 2, 3 |
|  | 14 |  |  | 6 |  |
|  | 15 |  |  | 7 |  |
|  | 16 |  |  | 8 |  |
| Fifth location | 17 | 5 |  | 9 | 2 | 2, 3, 4 |
|  | 18 |  |  | 10 |  |
|  | 19 |  |  | 11 |  |
|  | 20 |  |  | 12 |  |
| Sixth location | 21 | 6 |  | 13 | 2 | 3, 4, 5 |
|  | 22 |  |  | 14 |  |
|  | 23 |  |  | 15 |  |
|  | 24 |  |  | 16 |  |
| Seventh location | 25 | 7 |  | 1 | 3 | 4, 5, 6 |
|  | 26 |  |  | 2 |  |
|  | 27 |  |  | 3 |  |
|  | 28 |  |  | 4 |  |
| Eighth location | 29 | 8 |  | 5 | 3 | 5, 6, 7 |
|  | 30 |  |  | 6 |  |
|  | 31 |  |  | 7 |  |
|  | 32 |  |  | 8 |  |

As noted above, the above table is specific to the first game level in the game, which is different from subsequent game levels in that it has a slow ramp up for gaming elements, which allows the introduction of new game concepts and elements over time. Once the first game level is complete, subsequent levels may proceed as according to the following schedule, where "n" refers to the level number, e.g., 2 or 3.

TABLE 5

| Map 1 | Config. | Background | Layout | Power-ups | Treasures |
|---|---|---|---|---|---|
| First location | n + 1 | 1 | Hard | 1 | 1 | 1 |
|  | n + 2 |  |  | 2 |  |
|  | n + 3 |  |  | 3 |  |
|  | n + 4 |  |  | 4 |  |
| Second location | n + 5 | 2 |  | 5 | 1 | 1, 2 |
|  | n + 6 |  |  | 6 |  |
|  | n + 7 |  |  | 7 |  |
|  | n + 8 |  |  | 8 |  |
| Third location | n + 9 | 3 |  | 9 | 1 | 1, 2, 3 |
|  | n + 10 |  |  | 10 |  |
|  | n + 11 |  |  | 11 |  |
|  | n + 12 |  |  | 12 |  |
| Fourth location | n + 13 | 4 |  | 13 | 1 | 2, 3, 4 |
|  | n + 14 |  |  | 14 |  |
|  | n + 15 |  |  | 15 |  |
|  | n + 16 |  |  | 16 |  |
| Fifth location | n + 17 | 5 |  | 1 | 2 | 3, 4, 5 |
|  | n + 18 |  |  | 2 |  |
|  | n + 19 |  |  | 3 |  |
|  | n + 20 |  |  | 4 |  |
| Sixth location | n + 21 | 6 |  | 5 | 2 | 4, 5, 6 |
|  | n + 22 |  |  | 6 |  |
|  | n + 23 |  |  | 7 |  |
|  | n + 24 |  |  | 8 |  |
| Seventh location | n + 25 | 7 |  | 9 | 3 | 5, 6, 7 |
|  | n + 26 |  |  | 10 |  |
|  | n + 27 |  |  | 11 |  |
|  | n + 28 |  |  | 12 |  |
| Eighth location | n + 29 | 8 |  | 13 | 3 | 6, 7, 8 |
|  | n + 30 |  |  | 14 |  |
|  | n + 31 |  |  | 15 |  |
|  | n + 32 |  |  | 16 |  |

Game Board Layout

In some embodiments, the game board layout may change with every configuration change. The layout may begin simply as the participant is learning the game, and then become progressively harder to add interest and complexity to the game. Layouts specify or include the number, size, and color of tiles. For example, in one embodiment, easy layouts (e.g., 2 different versions) may include 36-50 tiles, and 2-3 colors. Medium layouts (e.g., 2 different versions) may include 50-85 tiles, and 4 colors. Hard layouts (e.g., 16 different versions) may include 85-110 tiles, and 5 colors. Of course, other layout schemes may be used as desired.

In one embodiment, the game may utilize a plurality of different backgrounds/locations representing "places" the participant visits during the game. For example, the backgrounds may be the ruins or locations on a map to which the participant seeks to travel. The backgrounds may essentially drive the story of the game, encouraging the participant to move through the exercise to discover the next ruin. Each game level may have a different background. In one embodiment, there may be three levels in the game, represented by Mayan, Oceania, and Pueblo Indian regions, although other regions, backgrounds, and themes may be used as desired, these being exemplary only.

When the participant has completed their last correct trial in a configuration, a large particle system effect (or other effect) may be released that signifies the completion of their goal. In addition, all the tiles may move off the screen (e.g., via animation), and a summary screen may be presented. The main portion of this screen may be occupied by a map specific to the current game level. The map may contain a specified number of milestone markers, e.g., separated by dashes, thus indicating a path with milestones. This summary screen is described in more detail below.

When a treasure tile is collapsed the icon of the tile may move (e.g., via animation) to a fixed location, e.g., on the left hand side of the screen. Each of the three treasure types may be lined up from left to right with the most common treasure type occupying the far left hand position. The additional treasure types may occupy the spaces from left to right based on how common they are. If there are less then three treasures in the game level then the treasure locations will be left empty.

Below each treasure type may be a number that represents how many of each treasure type has been accumulated. When a configuration starts these numbers may be set to 0. Each time a participant acquires a treasure icon the corresponding number may be incremented.

If the participant is in a time-constrained schedule, they will naturally exit the exercises when the timer reaches 0. If the participant is in the middle of a trial when the timer reaches 0, the participant may be allowed to complete the current trial, and may be awarded points. Any collapses that result from the trial may be resolved. Once this is complete the participant may be presented with a dialog box indicating that the allowed time has elapsed in this exercises. Of course, information related to the participant's progress may be saved so that next time the participant enters the exercise they will start in the same place. In some embodiment, a 'Next" button may be provided whereby the participant may move on to the next exercise."

If the last trial occurs on the same trail that marks the completion of the configuration, the participant may be presented with a configuration summary screen, where they can review their progress, after which they may be prompted to enter the next exercise.

If the participant is in a non-time constrained schedule, the timer may be set to 00:00 and may be grayed out. The participant may thus only be able to exit the exercises by accessing the side bar menu and clicking the exit button. At this point the participant's exercises data may be saved and the usual process for exiting an exercise followed.

When a participant returns to an exercise, having played it in a previous session, they may be presented with the same background, game board layout and stimulus configuration they were training with in the previous session. The new session may also keep track of the number of correct tiles, e.g., coins that the participant received. The scale (trial meter) may thus be set to reflect this progress by presenting the number of coins in the scale and positioning the scale in the proper location. In addition to this the number of treasures and the timer may be restored to the settings in effect at the end of the previous session.

In one embodiment, the final ZEST value for the configuration may be saved before exiting the exercise. If a participant is returning to a configuration they have played before then the adaptive measure for the configuration may start from the last record threshold value plus 25 to 50%. Thus, if the presentation time in a configuration were 10 ms, when the participant returns to that same configuration they may begin with a presentation time of 12.5 ms-15 ms. This holds true for participants who have completed the entire set of (e.g., 96) configurations and are returning to the exercise for a second time, and may also apply to participants who have finished the first half (e.g., 48) of the configurations and continue to repeat the confirmations in the second half of training.

Note that the specifics of the game may not need to be saved, e.g., the location of power-ups, treasure tiles, and the location of the individual tiles themselves may not need to be reconstructed.

In some embodiments, the participant may be permitted to continue the exercise after they have finished all of the stimulus configurations. For example, the participant may have the option to (re)start the exercises from the beginning. None of their previous data from the exercise may carry over to the restarted exercise, with the possible exception of the participant's assessment data, goal, and assessment history.

In one embodiment, when the participant starts the exercises for the second time they may begin on the second configuration as opposed to the first. The adaptive measure for each configuration may start from the last recorded threshold value for the configuration plus 25-50%. Thus, as above, if the presentation time in a configuration were 10 ms, when the participant returns to that same configuration they may begin with a presentation time of 12.5 ms-15 ms.

As noted above, when a configuration is complete the participant may be presented with a configuration summary screen. The summary screen may display a map that shows the participant where they are and how much further they need to go. A particle system effect (or some other graphical effect) may indicate the current completed segment on the map. The timer may be paused while the participant is reviewing their information on this screen, and the pause button may be active so the participant can exit the exercise at this point if desired.

As the participant completes each configuration one of the dashes on the map may be checked off to represent the completion of the configuration. Thus, each dash between the milestones may represent a configuration. The larger milestone markers may be denoted with images that represent different locations on the journey though the stimulus set. When a participant enters a new milestone they may be presented with a new background. Moreover, in some embodiments, the game board or grid may obtain new power-ups and may acquire new treasure tiles. Once all (e.g., 8) markers are filled the participant may move on to a new theme all together.

In some embodiments, in addition to the map, the summary screen may provide the participant with a summery of their progress in the configuration. This progress may be completely in the context of the game play elements and may include their score and the number of tiles they have collapsed or cleared. A participant may also see a list of achievements they have met in the configuration, e.g., in the form of a list of no more then three icons with titles that explain the significance of the achievement.

The participant may receive additional bonus points for each gold coin (correct trial) and treasure they have received or earned. These may be animated from the side menu bar into a container on the summary screen, and the points may accumulate as the coins and treasures hit their target. Point advancement may be accompanied with a sound, e.g., a "ding".

In one embodiment, all of this information may be stored in a "book" in the middle of the map. The participant may be able to click back and forward buttons to review their progress in different configurations. Each page may have a small icon in the upper left hand corner that indicates which game level the information represents. So for example if the participant is in the Oceania game level and they flip back to the Mayan game level the icon in the upper left hand corner may change to reflect the game level they are viewing.

Additionally, when a participant is flipping though the pages and crosses over from one game level to the next they may see a full page map that contextualizes the information they are about to see. So, for example, if the participant is flipping forward in the book and they leave the Mayan level to enter the Oceania level they may see the map associated with Oceania. If, on the other hand, they are flipping backwards in the book and move from Oceania to the Mayan level then they may see a full page map of the Mayan world before they see the information for the Mayan world.

In one embodiment, the bottom of the map may include a button marked "Continue" (or equivalent). Upon pressing this button, if the participant still has time left in the configuration they may be taken to the next stimulus configuration. If on the other hand there is no more time in the configuration the participant may be presented with a message indicating that the time for the configuration has elapsed or expired.

If the participant is in the final configuration for the game level, the words "completed" (or equivalent) may be displayed on the screen (possibly animated) after all of the points have been added up. Particle effects (or other effects) may highlight each of the milestones markers on the map and the text on the continue buttons may change to "advance to next level" (or equivalent). The participant may be able to review their progress in the configuration summery book before they continue on to the next level, as described above. In some embodiments, special messaging may be presented in or around the final screen of the exercise that explains what the participants options are for continuing the exercise.

Thus, in some embodiments, the visual sweep exercise may be included as part of a game, such as the block and tile matching games described above, although it should be noted that in other embodiments, other games may be used as desired.

It should also be noted that the particular exercises disclosed herein are meant to be exemplary, and that other repetition-based cognitive training exercises using visual stimuli with multiple stimulus sets may be used as desired, possibly in combination. In other words, the visual sweeps exercises described herein are but specific examples of cognitive training exercises using a computing system to present visual stimuli to a participant, record the participant's responses, and modify some aspect of the visual stimuli based on these responses, where these method elements are repeated in an iterative manner using multiple sets of stimuli to improve the participant's cognition, e.g., to improve ability of the participant to process visual information. Note particularly that such cognitive training using a variety of such visual stimulus-based exercises, possibly in a coordinated manner, is contemplated.

Those skilled in the art should appreciate that they can readily use the disclosed conception and specific embodiments as a basis for designing or modifying other structures for carrying out the same purposes of the present invention without departing from the spirit and scope of the invention as defined by the appended claims. For example, various embodiments of the methods disclosed herein may be implemented by program instructions stored on a memory medium, or a plurality of memory media.

We claim:

1. A method for successively stimulating a variety of preferentially tuned neurons in the early visual cortex to enhance visual sensory processing and cognition in a participant, utilizing a computing device to present visual stimuli training exercises based on visual sweeps, and to record responses from the participant, the method comprising:

providing first and second visual sweeps that use a Gabor sweep pattern, wherein the first and second visual sweeps are available for visual presentation to the participant;

sequentially visually presenting at least two visual sweeps to the participant utilizing either the first visual sweep, the second visual sweep, or a combination of the first and second visual sweeps;

requiring the participant to indicate an order in which the at least two visual sweeps were presented;

the computing device determining whether the participant indicated the order of the at least two visual sweeps correctly; and repeating said sequentially visually presenting, said requiring, and said determining one or more times in an iterative manner to improve the participant's cognition.

2. The method of claim 1, wherein the first visual sweep comprises a first orientation sweep which rotates counter-clockwise over time, and wherein the second visual sweep comprises a second orientation sweep which rotates clockwise over time.

3. The method of claim 2, wherein the step of repeating said sequentially visually presenting, said requiring, and said determining one or more times in an iterative manner also includes progressively adjusting one or more of:
a rate of the sweep;
cycles/deg for the sweep pattern;
size of the sweep's image; or
colors of the sweep pattern.

4. The method of claim 1, further comprising performing a plurality of spatial frequency sweep tasks and orientation sweep tasks.

5. The method of claim 4, wherein said performing a plurality of spatial frequency sweep tasks and orientation sweep tasks comprises:
performing trials for the spatial frequency sweep task and the orientation sweep task on respective alternate sessions.

6. The method of claim 4, wherein said performing a plurality of spatial frequency sweep tasks and orientation sweep tasks comprises:
performing trials under a first number of conditions for the spatial frequency sweep task, and under a second number of conditions for the orientation sweep task on first alternate sessions; and
performing trials under the second number of conditions for the spatial frequency sweep task, and under the first number of conditions for the orientation sweep task on second alternate sessions;
wherein the first alternate sessions and the second alternate sessions are interleaved.

7. The method of claim 1, wherein the visual sweeps dynamically modify a spatially periodic pattern.

8. The method of claim 7, wherein at least one of the visual sweeps changes an angular orientation of a periodic pattern over a time interval, thereby over the course of the sweep stimulating different neurons that are selectively tuned to specific orientations.

9. A non-transitory computer-readable memory medium that stores program instructions for successively stimulating a variety of preferentially tuned neurons in the early visual cortex to enhance visual sensory processing and cognition in a participant, utilizing a computing device to present visual stimuli training exercises based on visual sweeps, and to record responses from the participant, wherein the program instructions are executable by a processor to perform:

providing first and second visual sweeps that use a Gabor sweep pattern, wherein the first and second visual sweeps are available for visual presentation to the participant;

sequentially visually presenting at least two visual sweeps to the participant utilizing either the first visual sweep, the second visual sweep, or a combination of the first and second visual sweeps;

requiring the participant to indicate an order in which the at least two visual sweeps were presented;

determining whether the participant indicated the order of the at least two visual sweeps correctly; and repeating said sequentially visually presenting, said requiring, and said determining one or more times in an iterative manner to improve the participant's cognition.

10. A method for successively stimulating a variety of preferentially tuned neurons in the early visual cortex to enhance visual sensory processing and cognition in a participant, utilizing a computing device to present visual stimuli training exercises based on visual sweeps, and to record responses from the participant, the method comprising:

providing first and second spatial frequency sweeps, wherein the first spatial frequency sweep comprises a sweep pattern that increases in frequency over time, and wherein the second spatial frequency sweep comprises a sweep pattern that decreases in frequency over time, and wherein the first and second visual sweeps are available for visual presentation to the participant;

sequentially visually presenting at least two spatial frequency sweeps to the participant utilizing either the first spatial frequency sweep, the second spatial frequency sweep, or a combination of the first and second spatial frequency sweeps;

requiring the participant to indicate an order in which the at least two spatial frequency sweeps were presented;

the computing device determining whether the participant indicated the order of the at least two spatial frequency sweeps correctly; and repeating said sequentially visually presenting, said requiring, and said determining one or more times in an iterative manner to improve the participant's cognition.

11. The method of claim 10, further comprising:

associating the first spatial frequency sweep with a first icon; and associating the second spatial frequency sweep with a second icon;

wherein said requiring the participant to indicate the order in which the at least two spatial frequency sweeps were presented comprises requiring the participant to select one or more of the icons one or more times to indicate the order of the at least two spatial frequency sweeps.

12. The method of claim 11, wherein said associating the first spatial frequency sweep with a first icon comprises:

visually presenting the first spatial frequency sweep; and after said visually presenting the first spatial frequency sweep, highlighting the first icon to indicate to the participant the association; and wherein said associating the second spatial frequency sweep with a second icon comprises:

visually presenting the second spatial frequency sweep; and after said visually presenting the second spatial frequency sweep, highlighting the second icon to indicate to the participant the association.

13. The method of claim 11, wherein said requiring comprises:

receiving input from the participant selecting the icons in an order that indicates the order in which the at least two spatial frequency sweeps were presented, selection of the icons made by the participant placing a cursor over an icon and clicking a mouse, wherein each mouse click is recorded as a selection;

recording the selections made by the participant; and recording whether the participant correctly identified the order in which the at least two spatial frequency sweeps were presented.

14. The method of claim 10, wherein said sequentially visually presenting at least two spatial frequency sweeps comprises presenting a sequence of two spatial frequency sweeps comprising one of the following possible combinations: first spatial frequency sweep-first spatial frequency sweep, first spatial frequency sweep-second spatial frequency sweep, second spatial frequency sweep-first spatial frequency sweep, and second spatial frequency sweep-second spatial frequency sweep.

15. The method of claim 10, wherein said sequentially visually presenting comprises:

randomly selecting at least two spatial frequency sweeps to be presented, utilizing combinations of the first spatial frequency sweep and the second spatial frequency sweep.

16. The method of claim 10, wherein the first and second spatial frequency sweeps are each of a specified duration.

17. The method of claim 16, wherein said sequentially visually presenting separates the at least two spatial frequency sweeps by a specified inter-stimulus-interval (ISI).

18. The method of claim 17, wherein said sequentially visually presenting at least two spatial frequency sweeps comprises visually presenting the at least two spatial frequency sweeps at a specified stimulus intensity.

19. The method of claim 18, wherein said repeating comprises:

adjusting the stimulus intensity for said sequentially visually presenting based on whether the participant indicated the order of the at least two spatial frequency sweeps correctly;

wherein said adjusting is performed using a maximum likelihood procedure.

20. The method as recited in claim 19, wherein the maximum likelihood procedure comprises one or more of:

a QUEST (quick estimation by sequential testing) threshold procedure; or a ZEST (zippy estimation by sequential testing) threshold procedure.

21. The method of claim 20, wherein said adjusting the stimulus intensity comprises:

if the participant correctly indicates the order in which the at least two spatial frequency sweeps were presented, shortening the duration and/or the ISI.

22. The method of claim 18, wherein the stimulus intensity comprises a presentation time for each spatial frequency sweep, comprising the duration and/or the ISI.

23. The method of claim 18, wherein the stimulus intensity comprises one or more of:

size of the sweep's image;

rate of the sweep;

frequency range of the sweep;

a range of cycles/deg for the sweep; or the colors of the sweep pattern.

24. The method of claim 20, wherein said adjusting the stimulus intensity comprises:
if the participant incorrectly indicates the order in which the at least two spatial frequency sweeps were presented, lengthening the duration and/or the ISI.

25. The method of claim 20, wherein said adjusting the stimulus intensity comprises:
adjusting the stimulus intensity to approach and substantially maintain a specified success rate for the participant.

26. The method of claim 25, wherein said adjusting the stimulus intensity to approach and substantially maintain a specified success rate for the participant is performed for each of a plurality of visual sweep conditions.

27. The method of claim 25, wherein said adjusting the stimulus intensity to approach and substantially maintain a specified success rate for the participant uses a single staircase maximum likelihood procedure.

28. The method of claim 20, wherein said sequentially visually presenting, said requiring, and said determining composes performing a trial.

29. The method of claim 28, wherein said repeating comprises:
performing a plurality of trials under each of a plurality of visual sweep conditions, wherein each visual sweep condition specifies one or more attributes of the at least two spatial frequency sweeps.

30. The method of claim 29, wherein each of the visual sweep conditions specifies one or more of:
an orientation of the sweep pattern;
size of the sweep's image;
rate of the sweep;
frequency range of the sweep;
a range of cycles/deg for the sweep; or
the colors of the sweep pattern.

31. The method of claim 20, wherein said repeating comprises:
assessing the participant's performance a plurality of times during said repeating.

32. The method of claim 31, wherein said assessing the participant's performance a plurality of times is performed according to the maximum likelihood procedure.

33. The method of claim 32, wherein said assessing the participant's performance a plurality of times is performed using a 2-staircase maximum likelihood procedure.

34. The method of claim 10, further comprising:
indicating whether the participant indicated the order of the at least two spatial frequency sweeps correctly, wherein said indicating is performed audibly and/or graphically.

35. The method of claim 10, wherein said repeating occurs a number of times each day, for a number of days.

36. The method of claim 10, wherein said repeating is performed in the context of a game.

37. A non-transitory computer-readable memory medium that stores program instructions for successively stimulating a variety of preferentially tuned neurons in the early visual cortex to enhance visual sensory processing and cognition in a participant, utilizing a computing device to present visual stimuli training exercises based on visual sweeps, and to record responses from the participant, wherein the program instructions are executable by a processor to perform:
providing first and second spatial frequency sweeps, wherein the first spatial frequency sweep comprises a sweep pattern that increases in frequency over time, and wherein the second spatial frequency sweep comprises a sweep pattern that decreases in frequency over time, and wherein the first and second visual sweeps are available for visual presentation to the participant;
sequentially visually presenting at least two spatial frequency sweeps to the participant utilizing either the first spatial frequency sweep, the second spatial frequency sweep, or a combination of the first and second spatial frequency sweeps;
requiring the participant to indicate an order in which the at least two spatial frequency sweeps were presented;
determining whether the participant indicated the order of the at least two spatial frequency sweeps correctly; and
repeating said sequentially visually presenting, said requiring, and said determining one or more times in an iterative manner to improve the participant's cognition.

38. A method for successively stimulating a variety of preferentially tuned neurons in the early visual cortex to enhance visual sensory processing and cognition in a participant, utilizing a computing device to present visual stimuli training exercises based on visual sweeps, and to record responses from the participant, the method comprising:
providing first and second orientation sweeps, wherein the first orientation sweep comprises a sweep pattern that rotates counter-clockwise over time, and wherein the second orientation sweep comprises a sweep pattern that rotates clockwise over time, and wherein the first and second visual sweeps are available for visual presentation to the participant;
sequentially visually presenting at least two orientation sweeps to the participant utilizing either the first orientation sweep, the second orientation sweep, or a combination of the first and second orientation sweeps;
requiring the participant to indicate an order in which the at least two orientation sweeps were presented;
the computing device determining whether the participant indicated the order of the at least two orientation sweeps correctly; and
repeating said sequentially visually presenting, said requiring, and said determining one or more times in an iterative manner to improve the participant's cognition.

39. The method of claim 38, further comprising:
performing trials in one or more practice sessions for each of one or more orientation sweep tasks, wherein the one or more practice sessions comprise one or more of:
at least one single sweep session; and/or
at least one order task practice session.

40. A non-transitory computer-readable memory medium that stores program instructions for successively stimulating a variety of preferentially tuned neurons in the early visual cortex to enhance visual sensory processing and cognition in an participant, utilizing a computing device to present visual stimuli training exercises based on visual sweeps, and to record responses from the participant, wherein the program instructions are executable by a processor to perform:
providing first and second orientation sweeps, wherein the first orientation sweep comprises a sweep pattern that rotates counter-clockwise over time, and wherein the second orientation sweep comprises a sweep pattern that rotates clockwise over time, and wherein the first and second visual sweeps are available for visual presentation to the participant;
sequentially visually presenting at least two orientation sweeps to the participant utilizing either the first orientation sweep, the second orientation sweep, or a combination of the first and second orientation sweeps;
requiring the participant to indicate an order in which the at least two orientation sweeps were presented;

determining whether the participant indicated the order of the at least two orientation sweeps correctly; and repeating said sequentially visually presenting, said requiring, and said determining one or more times in an iterative manner to improve the participant's cognition.

41. A method for successively stimulating a variety of preferentially tuned neurons in the early visual cortex to enhance visual sensory processing and cognition in a participant, utilizing a computing device to present visual stimuli training exercises based on visual sweeps, and to record responses from the participant, the method comprising:

providing first and second visual sweeps that dynamically modify a spatially periodic pattern, wherein at least one of the visual sweeps increases or decreases the spatial frequency of a periodic pattern over a time interval, thereby presenting a frequency pattern that expands or contracts in spatial frequency, and thereby over the course of the sweep stimulating neurons that are selectively tuned to higher spatial frequencies and stimulating neurons that are selectively tuned to lower spatial frequencies, wherein the first and second visual sweeps are available for visual presentation to the participant;

sequentially visually presenting at least two visual sweeps to the participant utilizing either the first visual sweep, the second visual sweep, or a combination of the first and second visual sweeps;

requiring the participant to indicate an order in which the at least two visual sweeps were presented;

the computing device determining whether the participant indicated the order of the at least two visual sweeps correctly; and repeating said sequentially visually presenting, said requiring, and said determining one or more times in an iterative manner to improve the participant's cognition.

42. The method of claim 41, wherein the periodic pattern is characterized by gratings whose luminance varies spatially as a function of space or distance.

43. The method of claim 42, wherein the luminance varies between a maximum and minimum contrast determined as a function of an adjustable stimulus intensity level.

44. The method of claim 41, wherein the periodic pattern is characterized as a group of concentric circles having a regular pattern of radii.

45. The method of claim 41, wherein the periodic pattern is further modified by a multidimensional Gaussian window, whereby the periodic pattern becomes gradually fainter as a function of a distance from a center of the window.

* * * * *